US010502686B2

(12) United States Patent
Li et al.

(10) Patent No.: US 10,502,686 B2
(45) Date of Patent: Dec. 10, 2019

(54) SENSOR AND METHOD FOR DETECTING MERCURY

(71) Applicant: Griffith University, Nathan (AU)

(72) Inventors: Qin Li, Nathan (AU); Wentai Wang, Nathan (AU)

(73) Assignee: Griffith University, Nathan (AU)

( * ) Notice: Subject to any disclaimer, the term of this patent is extended or adjusted under 35 U.S.C. 154(b) by 40 days.

(21) Appl. No.: 15/323,467

(22) PCT Filed: Jul. 3, 2015

(86) PCT No.: PCT/AU2015/000390
§ 371 (c)(1),
(2) Date: Jan. 3, 2017

(87) PCT Pub. No.: WO2016/000031
PCT Pub. Date: Jan. 7, 2016

(65) Prior Publication Data
US 2017/0146456 A1    May 25, 2017

(30) Foreign Application Priority Data

Jul. 4, 2014 (AU) ................................ 2014902581

(51) Int. Cl.
| | |
|---|---|
| *B82Y 30/00* | (2011.01) |
| *C01B 32/05* | (2017.01) |
| *G01N 21/64* | (2006.01) |
| *C07F 7/18* | (2006.01) |
| *C09K 11/02* | (2006.01) |
| *C09K 11/65* | (2006.01) |
| *C09K 11/06* | (2006.01) |
| *B82Y 20/00* | (2011.01) |
| *B82Y 15/00* | (2011.01) |
| *B82Y 40/00* | (2011.01) |

(52) U.S. Cl.
CPC ............ *G01N 21/643* (2013.01); *B82Y 30/00* (2013.01); *C01B 32/05* (2017.08); *C07F 7/1804* (2013.01); *C09K 11/025* (2013.01); *C09K 11/06* (2013.01); *C09K 11/65* (2013.01); *B82Y 15/00* (2013.01); *B82Y 20/00* (2013.01); *B82Y 40/00* (2013.01); *G01N 2021/6432* (2013.01); *G01N 2021/6439* (2013.01); *Y10S 977/774* (2013.01); *Y10S 977/89* (2013.01); *Y10S 977/95* (2013.01); *Y10S 977/957* (2013.01)

(58) Field of Classification Search
CPC ........... G01N 33/0045; G01N 33/0036; G01N 33/0027; G01N 33/0009; G01N 33/0004; G01N 33/00; G01N 21/643; G01N 21/6428; G01N 21/64; G01N 21/625; G01N 21/62; C01F 7/184; C01F 7/1812; C01F 7/1804; C01F 7/18; C01F 7/08; C01F 7/00; C01B 32/05; B82Y 30/00
USPC ....................................................... 436/81, 73
See application file for complete search history.

(56) References Cited

U.S. PATENT DOCUMENTS

| | | | | |
|---|---|---|---|---|
| 2004/0167257 A1* | 8/2004 | Ryang | ................. | B82Y 30/00 524/262 |
| 2007/0141726 A1 | 6/2007 | Ying et al. | | |

FOREIGN PATENT DOCUMENTS

| | | |
|---|---|---|
| CN | 101551331 A | 10/2009 |
| CN | 103421495 A | 12/2013 |

OTHER PUBLICATIONS

Yang et al, Controllable Synthesis of Fluorescent Carbon Dot and the Detection Application as Nanoprobes, Nano-Micro Lett., 2013, 5(4), 247-259. (Year: 2013).*
Ma et al, Functionalization of carbon nanotubes using a silane coupling agent, Carbon, 2006, 44, 3232-3238. (Year: 2006).*
Guo et al, Hydrothermal synthesis of highly fluorescent carbon nanoparticles from sodium citrate and their use for the detection of mercury ions, Carbon, 2013, 52, 583-589. (Year: 2013).*
International Search Report and Written Opinion, International Application No. PCT/AU2015/000390, dated Sep. 8, 2015.
Li et al., Engineering surface states of carbon dots to achieve controllable luminescence for solid-luminescent composites and sensitive Be2+ detection, Sci. Rep., 4:4976 (2014).
Lu et al., Economical, green synthesis of fluorescent carbon nanoparticles and their use as probes for sensitive and selective detection of mercury(II) ions, Anal. Chem., 84:5351-7 (2012).
Wang et al., Carbon quantum dots: synthesis, properties and applications, J. Mater. Chem. C, 2:6921-39 (2014).
Wang et al., Highly luminescent organosilane-functionalized carbon dots, Adv. Funct. Mater., 21:1027-31 (2011).
Chinese patent application No. 201580047814.3, First Office Action, dated Dec. 13, 2018.

* cited by examiner

*Primary Examiner* — Christine T Mui
(74) *Attorney, Agent, or Firm* — Marshall, Gerstein & Borun LLP

(57) ABSTRACT

Organosilane functionalised carbon nanoparticles comprising a carbon dot bonded to an organosilane functionalization agent in a first orientation having one or more functional groups capable of binding mercury located at or proximal to a free end thereof.

19 Claims, 19 Drawing Sheets

SENSOR AND METHOD FOR DETECTING MERCURY

FIELD

The present invention relates to organosilane functionalised carbon nanoparticles and a method of preparing same. The present invention also relates to a sensor and method for detecting mercury using the organosilane functionalised carbon nanoparticles.

BACKGROUND

Carbon dots (CDs) are a class of carbon-based nanoparticles that comprise discrete carbogenic nanoparticles with sizes below 10 nm. CDs have emerged as versatile fluorescent nanoparticles possessing unique features such as high quantum yields, nontoxicity, nonblinking, high photostability and vast accessibility, with strong potential to be applied in bioimaging, sensing and optoelectronic devices. CDs can be synthesized through a number of methods including laser ablation, electrochemical exfoliation, carrier-supported aqueous route, combustion route, hot injection, hydrothermal treatment, microwave treatment, and so forth. These methods generally result in hydrophilic CDs with abundant —COOH and —OH groups on the surface of the CD, which are amenable for further functionalization.

Various functionalised CDs have been demonstrated as effective fluorescence probes for the detection of copper ions, ferric ions, silver ions, as well as mercury ions in water. The presence of the cation analyte quenches the CD fluorescence with the fluorescence intensity being proportional to the concentration of analytes, most likely due to the effect of electron transfer. In terms of $Hg^{2+}$ sensing, functionalised CDs provide many advantages such as high sensitivity, better water solubility, economic and green synthesis routes, convenient detection procedure, and compatibility with various sensing platforms such as optical fibre devices.

Notwithstanding the promising features of many functionalised CDs, there is still a need to improve the various properties of functionalised CDs in order for them to be employed in commercial and industrial applications. These improvements include simpler and more efficient synthetic methods, improved optical properties such as tunable emission bands and enhanced quantum yield (QY), heightened sensitivity, specificity and durability in complex fluids, such as wastewater effluent. Wastewater effluent, for example, contains large amounts of organic matter, bacteria and viruses; with an inherently high fluorescence background. Moreover, organic and biological matter is prone to interact or contaminate nanoparticle surfaces, representing a challenging sample type for fluorescence probes.

Despite being one of the most toxic heavy metal ions, mercury ($Hg^{2+}$) ion is widespread and widely used in industry, causing serious environmental and health concerns. With the maximum contamination limit for $Hg^{2+}$ in drinking water set at 2 ppb (~10 nM) by the United States Environmental Protection Agency, detection and remediation of $Hg^{2+}$ in water has always been a high priority area in environment and public health. The increased necessity and practice in wastewater recycling in recent years has further increased the urgency of developing facile and accurate $Hg^{2+}$ detection methods. The safety and public acceptance of the use of recycled wastewater demands monitoring of the presence and concentration of toxic chemicals, such as $Hg^{2+}$, in both wastewater and recycled water.

Many analytical methods for $Hg^{2+}$ detection have been developed including surface-enhanced Raman scattering (SERS) technique, surface plasmon resonances, inductively coupled plasma mass spectrometry, fluorescence chemosensors, electrochemical methods, and so forth. Among them, fluorescence-based sensing probes are desirable owing to several of their advantageous characteristics including high sensitivity, fast response, non-destructiveness and convenient operations. Most of the known $Hg^{2+}$ fluorescence probes are metal-based, such as gold and silver nanoparticles and nanowires. Organic molecules and semiconductor quantum dots have also been applied as fluorescence probes for $Hg^{2+}$ detection. The above fluorescence probes, however, possess several disadvantages which greatly limit their practical application, such as high production costs, toxicity of the probe materials, poor stability and complex synthesis procedures. Therefore, new $Hg^{2+}$ fluorescent probes that can overcome the above limitations are highly desirable. Any references to background art do not constitute an admission that the art forms a part of the common general knowledge of a person of ordinary skill in the art. The above references are also not intended to limit the application of the process and the system as disclosed herein.

SUMMARY

According to a first aspect, there is provided organosilane functionalised carbon nanoparticles comprising a carbon dot bonded to an organosilane functionalization agent in a first orientation having one or more functional groups capable of binding mercury located at or proximal to a free end thereof. In the first orientation, a fixed end of the organosilane functionalization agent may be bonded to the surface of the carbon dot with Si—O—Si and/or Si—O—C bonds. In one embodiment, the one or more functional groups capable of binding to mercury may be N-containing functional groups or S-containing functional groups.

In one embodiment, the one or more N-containing functional groups may comprise an amine group, preferably a chelating amine group. The chelating amine group may comprise a polyamine, such as an alkylenediamine or an alkylenetriamine. In one embodiment, the one or more S-containing functional groups may comprise a thiol group, Additionally, the carbon dots may be bonded to the organosilane functionalization agent in a second orientation, wherein one or more silane functional groups are located at or proximal to a free end thereof. In the second orientation, the fixed end of the organosilane functionalization agent may be bonded to the surface of the carbon dot via the one of more functional groups capable of binding mercury. For example, in embodiments where the one or more functional groups may be amine functional groups, the fixed end of the organosilane functionalization agent may be bonded via amidation of the one or more amine functional groups.

In one embodiment, the organosilane functionalised carbon nanoparticles comprise carbon dots having a first functionalization and a second functionalization, wherein the first functionalization comprises a long chain organic compound bonded to a surface of the carbon dot with Si—O—Si and/or Si—O—C bonds and having one or more amine functional groups located at or proximal to a free end thereof, and the second functionalization comprises a long chain organic compound bonded to the surface of the carbon dot via amidation and having one or more silane moieties located at or proximal to a free end thereof.

In view of the dual functionalization of the carbon dots, the organosilane functionalized carbon nanoparticles are amphiphilic. The organosilane functionalized carbon nanoparticles are dispersible in polar and apolar solvents.

The organosilane functionalized carbon nanoparticles are photoluminescent. In one embodiment, the quantum yield may be >20%, more particularly >40%. Furthermore, the organosilane functionalized carbon nanoparticles are excitation-independent.

The photoluminescence of organosilane functionalized carbon nanoparticles is quenched in the presence of mercury. The mercury can be Hg(0) or the mercury can be Hg(II) or $Hg^{2+}$. In one embodiment, the photoluminescence of organosilane functionalized carbon nanoparticles is selectively quenched by mercury, in particular $Hg^{2+}$. In one particular embodiment, the organosilane functionalized carbon nanoparticles have a detection range of 0-50 nM $Hg^{2+}$. In these embodiments, the organosilane functionalized carbon nanoparticles have a detection limit of <2 nM $Hg^{2+}$, more particularly a detection limit of 1.35 nM $Hg^{2+}$.

Accordingly, there is provided a photoluminescent sensor for mercury comprising organosilane functionalized carbon nanoparticles as described herein. The photoluminescent sensor for mercury may be employed in methods for detecting, and determining the concentration of, mercury in a sample.

The method of detecting the presence of mercury in a sample may comprise:
a) contacting a photoluminescent sensor as described herein with the sample;
b) irradiating the photoluminescent sensor at one or more excitation wavelengths and measuring the fluorescence intensity of the photoluminescent sensor, respectively, upon or after contact with the sample.

The system for detecting the presence of mercury in a sample may comprise a photoluminescent sensor as described herein, an excitation source for irradiating the photoluminescent sensor at one or more excitation wavelengths, and a detector for measuring fluorescence intensity of the photoluminescent sensor, respectively, upon or after contact with the sample.

The method of determining the concentration of mercury in a sample may comprise:
a) contacting a photoluminescent sensor as described herein with the sample;
b) irradiating the photoluminescent sensor at one or more excitation wavelengths and measuring the fluorescence intensity of the photoluminescent sensor, respectively, upon or after contact with the sample; and,
c) comparing the measurement obtained in step b) with that of a calibration curve created using known concentrations of mercury.

The system for determining the concentration of mercury in a sample may comprise a photoluminescent sensor as described herein, an excitation source for illuminating the photoluminescent sensor at one or more excitation wavelengths, a detector for measuring fluorescence intensity of the photoluminescent sensor upon or after contact with the sample. and a calibration curve created using known concentrations of mercury.

The systems and method described above may employ a photoluminescent device comprising the photoluminescent sensor as described herein dispersed into a solution. The systems and method described above may employ a photoluminescent device comprising the photoluminescent sensor as described herein immobilised on a substrate. In one particular embodiment, the substrate may be optical fibres.

In a further aspect there is provide the use of an organosilane functionalised carbon nanoparticle as described herein as a sensor for mercury in a gas stream or mercury dispersed in a liquid.

The organosilane functionalized carbon nanoparticles may be produced with a solvothermal process. A method of preparing organosilane functionalized carbon nanoparticles as described above may comprise heating a mixture of a precursor material and a functionalization agent in a closed vessel, wherein the functionalization agent comprises a long chain organic compound having one or more functional groups capable of binding mercury located at or proximal to a first terminal end and one or more silane functional groups or moieties located at or proximal to a second terminal end thereof. In one embodiment, the mixture is heated to a temperature in a range of 120° C.-180° C., preferably in a range of 140° C.-160° C.

BRIEF DESCRIPTION OF THE FIGURES

Notwithstanding any other forms which may fall within the scope of the sensor and methods as set forth in the Summary, specific embodiments will now be described, by way of example only, with reference to the accompanying figures in which.

DETAILED DESCRIPTION

Figure 1:
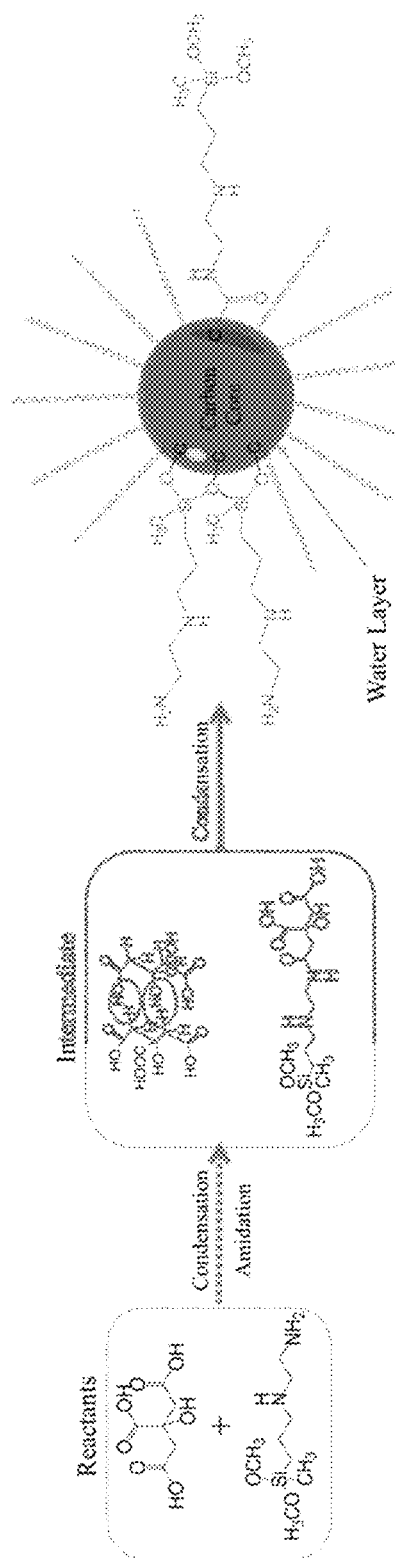
FIG. 1 is a reaction scheme in accordance with one embodiment.

In one aspect, the present application relates to organosilane functionalised carbon nanoparticles.

Organosilane Functionalised Carbon Nanoparticles

The term "carbon nanoparticles" is used to broadly refer to particles substantially comprising a carbon-based material having a particle size less than 10 nm. Illustrative examples of carbon-based materials include, but are not limited to, amorphous carbon, semi-crystalline carbon, crystalline carbon, graphitic carbon, graphene-like carbon, carbogenic compounds, and carbogenic oligomers. It will be understood that the carbon-based material may be doped or enriched with heteroatoms, such as N, B, S, F, O, P, Si and so forth, by using a carbogenic precursor material which contains said heteroatoms.

The term "functionalised carbon nanoparticle" is used to broadly refer to carbon nanoparticles whose surface is bonded to one or more functionalization agents via primary or secondary bonding interactions with terminal functional groups on the surface of the carbon nanoparticle. In this way, the functionalization agents become "anchored" or bound to the surface of the carbon nanoparticle.

The one or more functionalization agents may be a long chain organic compound having functional groups and/or moieties capable of forming primary bonding and/or secondary bonding interactions with terminal groups on the surface of the carbon nanoparticle. In general, such functional groups and/or moieties are located at or proximal to a terminal end of the long chain organic compound to facilitate formation of primary or secondary bonding interactions with terminal groups on the surface of the carbon nanoparticle.

"Organosilane functionalised carbon nanoparticles" refer to carbon nanoparticles which have been functionalised with an organosilane functionalization agent (i.e. long chain organic compounds with Si—O—Si and/or Si—O—C functional groups and/or moieties located at or proximal to a terminal end thereof). The surface of the resulting organosilane functionalised carbon nanoparticle has primary and/or secondary bonding interactions with the Si—O—Si and/or Si—O—C functional groups and/or moieties of the long chain organic compound.

The organosilane functionalised carbon nanoparticles described herein comprise carbon dots bonded to an organosilane functionalization agent in a first orientation having one or more functional groups capable of binding to $Hg^{2+}$ located at or proximal to a free end thereof. It will be understood that, in the first orientation, a fixed end of the organosilane functionalization agent may be bonded to the surface of the carbon dot with Si—O—Si and/or Si—O—C bonds. The one or more functional groups capable of binding to $Hg^{2+}$ may be N-containing functional groups or S-containing functional groups. Illustrative examples of N-containing functional groups include, but are not limited to, amine functional groups. Illustrative examples of S-containing functional groups include, but are not limited to, thiols.

In one embodiment, the one or more amine functional groups may comprise a chelating amine group. The chelating amine group may comprise a polyamine, such as an alkylenediamine or an alkylenetriamine.

Additionally, the carbon dots may be bonded to the organosilane functionalization agent in a second orientation, wherein one or more silane functional groups are located at or proximal to a free end thereof. It will be understood that, in the second orientation, the fixed end of the organosilane functionalization agent may be bonded to the surface of the carbon dot via amidation of the one or more amine functional groups.

Accordingly, the organosilane functionalised carbon nanoparticles described herein may be "dual functionalised" as depicted in FIG. 1.

In other words, the organosilane functionalised carbon nanoparticles may comprise carbon dots having a first functionalization and a second functionalization, wherein the first functionalization comprises a long chain organic compound bonded to a surface of the carbon dot with Si—O—Si and/or Si—O—C bonds and having one or more amine functional groups and/or one or more thiol functional groups located at or proximal to a free end thereof, and the second functionalization comprises a long chain organic compound bonded to the surface of the carbon dot via amidation and having one or more silane moieties located at or proximal to a free end thereof.

Carbon dots are carbon nanoparticles with an aspect ratio in a range of 0.9-1.1. The organosilane functionalised carbon nanoparticles prepared in accordance with the methods disclosed herein may have a particle size in a range of about 0.1 nm to about 5 nm, preferably in a range of 0.5 to 3 nm.

In view of the dual functionalization of the carbon dots, the organosilane functionalized carbon nanoparticles are amphiphilic. The organosilane functionalized carbon nanoparticles are dispersible in polar, apolar and nonpolar solvents. Illustrative examples of polar solvents include, but are not limited to, water, methanol and ethanol. Illustrative examples of apolar solvents include, but are not limited to, DMSO, DMF and acetone. Illustrative examples of nonpolar solvents include, but are not limited to THF, toluene and hexane.

Preparing Organosilane Functionalised Carbon Nanoparticles

The organosilane functionalized carbon nanoparticles may be produced with a solvothermal process.

A method of preparing organosilane functionalized carbon nanoparticles as described herein may comprise heating a mixture of a precursor material and a functionalization agent in a closed vessel, wherein the functionalization agent comprises a long chain organic compound having one or more functional groups capable of binding mercury located at or proximal to a first terminal end and one or more silane functional groups or moieties located at or proximal to a second terminal end thereof.

In one embodiment, the closed vessel may be an autoclave.

The mixture may be heated to a temperature in a range of 120° C.-180° C., preferably in a range of 140° C.-160° C.

In general the method of preparing organosilane functionalized carbon nanoparticles may be performed in a period up to 24 hours, preferably in a period up to about 4-6 hours. It will be appreciated that reactions performed at lower temperatures of 120° C. are likely to proceed to completion in periods of 12-24 hours, whereas reactions performed at higher temperatures are likely to proceed to completion in periods of 4-6 hours or less.

The inventors contrast the present method of preparation with other synthetic methods for organosilane functionalized carbon nanoparticles in which precursor material is reacted with a functionalization agent at high temperatures (i.e. 240° C.) in an open system. The resulting organosilane functionalized carbon nanoparticles comprise carbon dots having a single functionalization bonded to the surface of the carbon dot with one or more silane moieties located at or proximal to a free end thereof. These organosilane functionalised carbon nanoparticles are hydrophobic.

The inventors opine that the difference between the two synthetic strategies is that in the method disclosed herein, the reaction vessel is closed. Therefore, when the precursor material is transformed into the carbon dot, water released therefrom is trapped under pressure and, moreover, may reside at the interface between the surface of the carbon dot and the functionalization agent through hydrogen bonding interactions, thus facilitating formation and retention of these hydrophilic functional groups (e.g. —OH and —COOH). Furthermore, the organosilane functional groups, in particular the alkoxysilane functional groups, may be hydrolyzed within a thin water layer at the surface of the carbon dot, thereby attaching the functionalization agent to the surface of the carbon dot through Si—O—Si and Si—O—C bonding interactions. A general synthetic procedure is illustrated in FIG. 1.

Precursor Material

The "precursor material" may be any suitable organic chemical or organic material which can be converted by a solvothermal process into carbon dots. Illustrative examples of suitable organic compounds for use as the precursor material include, but are not limited to, organic acids such as citric acid, amino acids such as aspartic acid, aminopolycarboxylic acids, stearic acid; carbohydrates such as monosaccharides, disaccharides, oligosaccharides, and polysaccharides; polyhydroxy-substituted aldehydes; polyhydroxy-substituted ketones; polyols; heterocyclic compounds including heterocyclic bases and heterocyclic acids; mono- and polyunsaturated hydrocarbons; organic acids including, but not limited to, monofunctional or polyfunctional carboxylic acids and/or anhydrides, in particular polyhydroxy-substituted carboxylic acids and/or anhydrides; and heteroatom-substituted oligomers or polymers of ethylene oxide such as $PEG_{1500N}$.

As used herein, the term 'carbohydrate' generally refers to aldehyde or ketone compounds substituted with multiple hydroxyl groups, of the general formula $(CH_2O)_n$, wherein n is 2-36, as well as their oligomers and polymers. The carbohydrates of the present invention can in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phophonyl, phphinyl, phosphory, phosphino, thioester, thioether, oximino, hydrazine, carbamyl, phospho, phosphonato, boro, silyl, or any other viable functional group.

Non-limiting examples of suitable carbohydrates which may be used as the precursor material herein include glucose, fructose, galactose, xylose, ribose, sucrose, laculose, lactose, maltose, trehalose, cellobiose, raffinose, melezitose, maltotriose, acarbose, sachyose, fructooligosaccharides, galactooligosaccharides, mannon-oligosaccharides, cyclodextrin, cellulose.

A heterocyclic compound is a cyclic compound which has atoms of at least two different elements as members of its ring(s). The heterocyclic compounds used in the present invention contains at least one carbon atom, and one or more atoms of elements other than carbon with the ring structure, such as sulfur, oxygen or nitrogen.

Heterocyclic bases are organic compounds comprising an aromatic ring in which a lone pair of electrons of a ring-heteroatom (e.g. N, B, S, F, O, P, Si and so forth) is not part of the aromatic system and extends in the plane of the ring. The heterocyclic bases of the present invention can in addition, be substituted at one or more positions or fused with one or more aromatic rings. The heterocyclic bases optionally can be substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphory, phosphino, thioester, thioether, oximino, hydrazine, carbamyl, phospho, phosphonato, boro, silyl, or any other viable functional group.

Non-limiting examples of heterocyclic bases which may be used as the precursor material herein include pyridine, acridine, pyrazine, quinoxaline, quinoline, isoquinoline, pyrazole, indazole, pyrimidine, quinazoline, pyridazine, cinnoline, triazine, melamine, and derivatives and combinations thereof.

Heterocyclic acids used in the present invention are organic compounds comprising an aromatic ring in which a ring heteroatom may be part of the aromatic ring system and which has an acidic functional group directly or indirectly coupled to the aromatic ring system. For example, hydroxyl groups directly coupled to the aromatic ring by virtue of substitution of the C-ring atoms have acidic functionality. The heterocyclic acids of the present invention can in addition, be substituted at one or more positions or fused with one or more aromatic rings. The heterocyclic acids optionally can be substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphory, phosphino, thioester, thioether, oximino, hydrazine, carbamyl, phospho, phosphonato, boro, silyl, or any other viable functional group.

Non-limiting examples of heterocyclic acids which may be used as the precursor material herein include cyanuric acid.

Mono- and unsaturated hydrocarbons used as a precursor material in the present invention are organic compounds comprising a C2-C36 backbone with one or more C=C bonds. The mono- and unsaturated hydrocarbons of the present invention can in addition, be substituted at one or more positions with one or more moieties such as alkyl, halogen, haloalkyl, carboxyl acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphory, phosphino, thioester, thioether, oximino, hydrazine, carbamyl, phospho, phosphonato, boro, silyl, or any other viable functional group.

Monofunctional carboxylic acids as used herein as the precursor material are organic acids comprising a carboxylic acid group and optionally one or more functional groups, including functionalised and non-functionalised carboxylic acids. Monofunctional carboxylic acids useful herein, can be aliphatic, aromatic, saturated, linear and/or branched. The preferred monofunctional carboxylic acids have from about four to about twenty-four carbon atoms. The functionalised monofunctional carboxylic acids can be substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazine, carbamyl, phospho, phosphonato, boro, silyl, or any other viable functional group.

Non-limiting examples of suitable monofunctional carboxylic acids which may be used as the precursor material herein include isobutyric acid, benzoic acid, 2-ethyl butyric acid, hexanoic acid, heptanoic acid, 2-ethylhexanoic acid, octanoic acid, nonanoic acid, 3,5,5-trimethylhexanoic acid, isononanoic acid, decanoic acid, isooctadecanoic acid, dodecanoic acid, 2-methyl butyric acid, isopentanoic acid, pentanoic acid, 2-methyl pentanoic acid, 2-methyl hexanoic acid, isooctanoic acid, undecylinic acid, isolauric acid, isopalmitic acid, isostearic acid, behenic acid, and derivatives and combinations thereof.

The polyfunctional carboxylic acid is a carboxylic acid with at least two carboxylic acid groups and optionally one or more additional functional groups, including functionalized and non-functionalized dicarboxylic acids. Polyfunctional carboxylic acids and/or anhydrides can be aliphatic, aromatic, saturated, linear and/or branched. Preferably, the polyfunctional carboxylic acids and/or anhydrides used herein have one to about thirty six carbon atoms. The functionalised polyfunctional carboxylic acids can be substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazine, carbamyl, phospho, phosphonato, boro, silyl, or any other viable functional group.

Non-limiting examples of polyfunctional carboxylic acids and/or anhydrides which may be used as the precursor material herein include carbonic acid, hexanedioic acid, dimer acid, azelaic acid, sebacic acid, dodecanedioic acid, glutaric acid, succinic acid, citric acid, phthalic acid, isophthalic acid, terephthalic acid, 2,6-naphthalene dicarboxylic acid, and derivatives and combinations thereof.

Functionalisation Agent

The functionalization agent comprises a long chain organic compound having one or more functional groups capable of binding to mercury located at or proximal to a first terminal end and one or more silane functional groups or moieties located at or proximal to a second terminal end thereof.

In one embodiment, the one or more functional groups capable of binding to mercury may be N-containing functional groups or S-containing functional groups. In one embodiment, the one or more N-containing functional groups may comprise an amine group, preferably a chelating amine group. The chelating amine group may comprise a polyamine, such as an alkylenediamine or an alkylenetriamine. In one embodiment, the amine group is an imidazolidione.

The functionalization agent may comprise an organofunctional alkoxysilane, in particular an amino silane. Illustrative examples of suitable amino silanes include, but are not limited to, N-(2-aminoethyl)-3-aminopropylmethyldimethoxysilane (AEAPMS), N-(2-aminoethyl)-3-aminopropyltrimethoxysilane, 3-aminopropyltrimethoxysilane, 3-aminopropylmethyldimethoxysilane, 3-aminopropyltriethoxysilane, 3-aminopropyldiethoxymethylsilane, 3-aminopropyldimethylethoxysilane, (N-trimethoxysilylpropyl)polyethyleneimine; trimethoxylsilylpropyldiethylenetriamine; 3-[2-(2-aminoethylamino) ethylamino]propyl-trimethoxysilane, 3-(2-aminoethylamino)propylmethyldimethoxysilane (AEPMS), 3-(imidazolidin-2-on-1-yl)propylmethyldimethoxysilane (IPMS).

Alternatively, the functionalization agent may comprise an oligomer or a polymer with amine or thio functional groups located at or proximal to a terminal end thereof or in the structure thereof.

In one particular embodiment, the functionalization agent comprises N-(β-aminoethyl)-γ-aminopropylmethyldimethoxysilane (AEAPMS).

Photoluminescent Organosilane Functionalised Carbon Nanoparticles

The organosilane functionalized carbon nanoparticles described herein are photoluminescent. The term 'photoluminescent' refers to the ability of a functional group and/or moiety in a chemical substance to absorb energy of a specific wavelength and re-emit energy at a different (but equally specific wavelength). The amount and wavelength of the emitted energy depend on the functional group and/or moiety and its chemical environment.

The organosilane functionalized carbon nanoparticles described herein have an absorption peak in the UV-visible absorption spectrum and an emission peak in the UV-visible emission spectrum. The inventors note that some embodiments of the organosilane functionalized carbon nanoparticles are excitation-independent. In particular, in these embodiments, no noticeable position shift in emission peaks was observed when the excitation wavelength was varied in the range of 320-420 nm.

The photoluminescent lifetime of some embodiments of the organosilane functionalized carbon nanoparticles may be in a range from 2 ns to 20 ns, in particular 15 ns. The inventors ascribe the extraordinary long photoluminescence lifetime compared to other carbon dots as likely due to the abundant long chain surface functional groups which provide a better trapping effect.

In one embodiment, the quantum yield may be >20%, more particularly >40%. In some embodiments, the quantum yield is 50%.

The photoluminescent intensity of the organosilane functionalized carbon nanoparticles may not vary with ionic strength (NaCl), although the photoluminescent intensity can be pH-sensitive in weak acidic environments. For example, the photoluminescent intensity of the organosilane functionalized carbon nanoparticles can increase linearly with increase in pH from 1 to 5. Accordingly, the organosilane functionalized carbon nanoparticles as described herein may be employed as a pH probe for weak acidic solutions.

Mercury Sensitive Organosilane Functionalised Carbon Nanoparticles

The photoluminescence of organosilane functionalized carbon nanoparticles may be quenched in the presence of mercury. The mercury can be in a gas stream or is a liquid. The mercury is, in particular $Hg^{2+}$.

Figure 2:
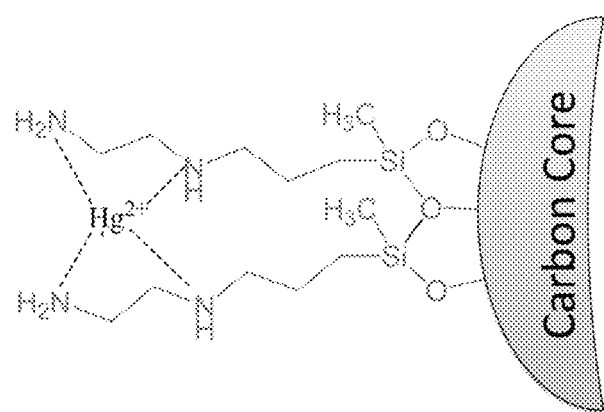
FIG. 2 is an embodiment of mercury bonding to an organosilane functionalise carbon nanoparticle.

The organosilane functionalized carbon nanoparticles as described herein can show a significantly better sensitivity to $Hg^{2+}$ than that of organosilane functionalised carbon nanoparticles prepared by previous methods. As depicted in FIG. 1, the organosilane functionalized carbon nanoparticles as described herein have amine-terminated alkylene chains due to the silane reaction with the carbon surface of the carbon dot. It is known that the binding affinity between $Hg^{2+}$ and $-NH_2/-NH$ groups is stronger than that between $Hg^{2+}$ and hydroxyl or carboxylate groups. Moreover, the spatial distribution of the terminal ethylene diamine is very likely to chelate $Hg^{2+}$ in a polyaza-$Hg^{2+}$ complex, as illustrated in FIG. 2. The metal complexation would facilitate the non-radiative electron/hole recombination annihilation through an effective electron transfer process, causing fluorescence quenching.

In one embodiment, the photoluminescence of organosilane functionalized carbon nanoparticles is selectively quenched by mercury, in particular $Hg^{2+}$. In one embodiment, the binding of mercury is reversible.

In one particular embodiment, the organosilane functionalized carbon nanoparticles have a detection range of 0-50 nM $Hg^{2+}$. In these embodiments, the organosilane functionalized carbon nanoparticles have a detection limit of <2 nM $Hg^{2+}$, more particularly a detection limit of 1.35 nM $Hg^{2+}$.

Accordingly, the organosilane functionalized carbon nanoparticles as described herein may be employed as a photoluminescent sensor for mercury, in particular $Hg^{2+}$. The photoluminescent sensor for mercury may be employed in a method and system for detecting mercury in a sample.

Method and System for Detecting the Presence of Mercury in a Sample

The term 'sample' as used herein may refer to any substance. Examples of "substances" include gases, fluids, liquids, solutions, solids, gels, polymers, and so forth. The substance may comprise one or more components. As an example, in the case of fluid or liquid substances, the substance may comprise a solvent (which may be a liquid, such as water or organic solvent), containing one or more solutes, ions or otherwise.

In particular the sample may be a water sample or an aqueous solution. Illustrative examples of water samples include, but are not limited to, potable water, municipal water, rainwater, storm water, wastewater, grey water, surface water, industrial process water, deionized water, ultrapure water, distilled water, desalinated water, stock water, irrigation water, groundwater, seawater, saline water, brine, brackish water, produced water, process water, recycled and/or treated water, tailings dam water, settling pond water, and so forth.

The sample may also be a biological fluid, such as blood, blood plasma, urine, bile fluids, and so forth.

The method of detecting the presence of mercury in a sample may comprise:
a) contacting a photoluminescent sensor as described herein with the sample;
b) irradiating the photoluminescent sensor at one or more excitation wavelengths and measuring the fluorescence intensity of the photoluminescent sensor, respectively, upon or after contact with the sample.

Contacting the Photoluminescent Sensor

Contacting the photoluminescent sensor as described herein with the sample may be performed by any suitable technique and for a sufficient period of time to allow the organosilane functionalised carbon nanoparticles to react with and bind any mercury residing in the sample. The technique used to contact the photoluminescent sensor will depend, to an extent, on the sample.

For example, the photoluminescent sensor may be immersed in the sample. In other embodiments, the sample may be topically applied to the photoluminescent sensor, typically by spraying said sample on the photoluminescent sensor. In still further embodiments, the photoluminescent sensor may be disposed in a flow stream of the sample.

The sensor may be suspended or immobilised in the sample. The sensor can comprise disperse particles of the sensor in the sample. The sensor may be a solid having at least one surface that contacts the sample. The sensor can be adapted to increase the surface area, e.g. by comprising a porous surface.

In some embodiments, a period of up to 30 minutes may be required for the organosilane functionalised carbon nanoparticles to react with and bind any mercury residing in the sample. Accordingly, the method may comprise the step of contacting the photoluminescent sensor with the sample for a period of up to about 5, 10, 15, 20 or 30 minutes.

It will be appreciated, that in some embodiments, the sample may require preparation or pretreatment prior to contacting the photoluminescent sensor with the sample. Sample preparation or pretreatment may be achieved by employing a wide range of techniques, as will be known to the skilled person, with the objective of removing potential interferences, increasing the concentration of an analyte (e.g. $Hg^{2+}$), providing a robust, reproducible method that is independent of variations in the sample matrix. Such preparation, particularly in connection with wastewater, may comprise filtration and/or centrifugation to remove solids, pretreatment with flocculents and/or coagulents.

For example, ferric ions ($Fe^{3+}$) in the sample may also induce quenching of the photoluminescence intensity of the organosilane functionalized carbon nanoparticles as described herein, thereby masking the presence of mercury in the sample. A masking agent, such as sodium hexametaphosphate, may be added to the sample to counter the presence of ferric ions in the sample.

Similarly, cupric ions ($Cu^{2+}$) may also induce quenching of the photoluminescence intensity of the organosilane functionalized carbon nanoparticles as described herein. A masking agent, such as EDTA or thiourea, may be added to the sample to counter the presence of cupric ions in the sample.

Irradiating the Photoluminescent Sensor at One or More Excitation Wavelengths

Irradiating the photoluminescent sensor at one or more excitation wavelengths and measuring the fluorescence intensity of the photoluminescent sensor may be performed upon or after contact with the sample.

The term 'irradiating' is used broadly to refer to applying electromagnetic radiation. The term 'excitation wavelength' refers to the wavelength of electromagnetic radiation capable of causing the photoluminescent sensor to emit photoluminescence at one or more wavelengths when irradiated therewith. Generally, the excitation wavelength may be in the UV-visible spectrum.

Measuring the fluorescence intensity of the photoluminescent sensor may be undertaken with any suitable detector capable of measuring fluorescence intensity, such as a fluorescence detector. Illustrative examples of suitable fluorescence detectors include, but are not limited to, a CCD camera, a photon multiplier, or an opto-electric signal converter.

Fluorescence intensity may be measure at one or more wavelengths corresponding to the one or more wavelengths at which the photoluminescent sensor fluoresces. In the presence of mercury, in particular $Hg^{2+}$, the fluorescence intensity of the photoluminescent sensor as described herewith will decrease.

System for Detecting the Presence of Mercury

The system for detecting the presence of mercury in a sample may comprise a photoluminescent sensor as described herein, an excitation source for irradiating the photoluminescent sensor at one or more excitation wavelengths, and a detector for measuring fluorescence intensity of the photoluminescent sensor, respectively, upon or after contact with the sample.

In one embodiment, the photoluminescent sensor may be suspended in solution. In one embodiment, the sensor is immobilised on a substrate, thereby comprising a solid state photoluminescent device. The device can be handled in the solid state. In one embodiment, the sensor is dried on a flat surface and then extracted after aging. The extracted product can be a free-standing film. The substrate onto which the sensor is deposited may be any suitable material capable of binding to or supporting the organosilane functionalised carbon nanoparticles as described herein. For example, the substrate may be optical fibres, glass, transparent metal oxides. Optical fibres are particularly preferred because the optical fibres may be configured to be in operative communication with the detector, thereby serving as a conduit for light emission from the photoluminescent sensor to the detector.

The substrate may be prepared, prior to immobilisation of the organosilane functionalised carbon nanoparticles thereon, to facilitate binding of said nanoparticles to the substrate. For example, the surface of the substrate may be cleaned, etched and/or pre-treated to provide a surface covered with Si—OH groups.

The photoluminescent sensor may be immobilised on the substrate in one or more layers. The substrate may be immersed in a solution of the organosilane functionalised carbon nanoparticles for a period of time sufficient to deposit a layer of said nanoparticles thereon. This process could be repeated to give multiple layers. It will also be appreciated that each layer of said nanoparticles may be interposed with an intermediate material. In some embodiments, the intermediate material may be a polymeric material.

In an alternative embodiment, the surface of the substrate may be prepared to provide one or more areas thereon disposed in a pattern. For example, one or more areas of the surface may be prepared to facilitate hydrophilic binding, while the remaining areas on the surface may be prepared to facilitate hydrophobic binding, or vice versa. The organosilane functionalised carbon nanoparticles bind in a different manner (e.g. varying extent) in the one or more areas. In this way, the patterned surface may facilitate multi-tasks being performed, such as calibration, measurement, false positive elimination, and so forth.

In another embodiment, the substrate may be first coated with a porous (meso to macro) material, such as a porous silica film. The organosilane functionalised carbon nanoparticles may be immobilised in the pores of the porous material. Advantageously, the higher surface area of the porous material facilitates an increased loading of organosilane functionalised carbon nanoparticles, providing better dispersivity for said carbon nanoparticles on the substrate, as well as an increased surface are for contact with analytes, such as $Hg^{2+}$.

Figure 9:
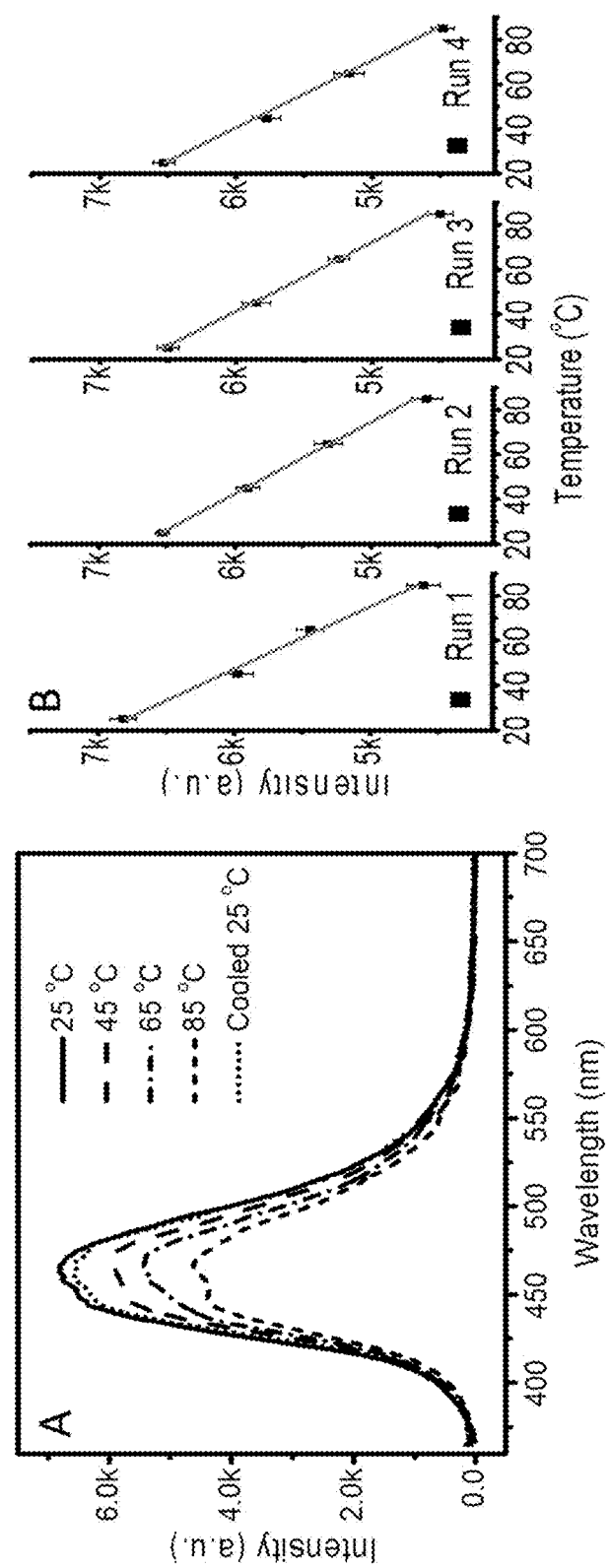
FIG. 9A shows photoluminescence emission spectra of as-prepared OS-CDs in aqueous solution at various temperatures and FIG. 9B shows the fitting curve of photoluminescence intensity changes at various temperatures under heating and cooling cycle running.

The organosilane carbon nanoparticles as described herein demonstrate temperature-dependent fluorescence intensity change (see FIGS. 9A & 9B). In one embodiment, a photoluminescent sensor device may be configured in a manner whereby the photoluminescence intensity may be converted to an electrical signal by providing a reference well which utilises the electrical energy for elevating the temperature which is adjusted by supplied voltage. The photoluminescence intensity correspondence can then be translated to electric voltage signal.

In one embodiment, the photoluminescent sensor may be immobilised onto a particulate substrate, thereby comprising a particulate photoluminescent device. The substrate may comprise particles of any of the aforementioned materials The substrate may comprise polystyrene particles. The surfaces of the particles can be functionalised by a swelling-diffusion-deswelling process. Once functionalised, the particles can be allowed to self-assemble into a structure. The structure can be an ordered structure. The ordered structure may contribute to enhancement of the fluorescence signal, thereby improving the sensing sensitivity.

Excitation Source

The excitation source applies electromagnetic radiation (or irradiates) the photoluminescent sensor, upon or after contact with the sample. In one embodiment, the excitation source is capable of irradiating the photoluminescent sensor at one or more excitation wavelengths in the UV-visible spectrum.

Detector

The detector may be any suitable fluorescence detector as will be known to the skilled person. In one embodiment, the fluorescence detector is capable of detecting one or more emission wavelengths in the UV-visible spectrum. Illustrative examples of suitable fluorescence detectors include, but are not limited to, a CCD camera, a photon multiplier, or an opto-electric signal converter.

Similarly, the photoluminescent sensor for mercury may be employed in a method and system for determining the concentration of mercury in a sample.

Methods and System for Determining the Concentration of Mercury in a Sample
a) The method of determining the concentration of mercury in a sample may comprise:
b) contacting a photoluminescent sensor as described herein with the sample;
c) irradiating the photoluminescent sensor at one or more excitation wavelengths and measuring the fluorescence intensity of the photoluminescent sensor, respectively, upon or after contact with the sample; and,
d) comparing the measurement obtained in step b) with that of a calibration curve created using known concentrations of mercury.

The system for determining the concentration of mercury in a sample may comprise a photoluminescent sensor as described herein, an excitation source for irradiating the photoluminescent sensor at one or more excitation wavelengths, a detector for measuring fluorescence intensity of the photoluminescent sensor upon or after contact with the sample and a calibration curve created using known concentrations of mercury.

The calibration curve may be pre-determined using known concentrations of mercury.

EXAMPLES

Non-limiting examples of a sensor and method of detecting mercury will now be described.

Example 1: Synthesis of Organosilane Functionalized Carbon Nanoparticles (OS-CDs)

Citric acid acid anhydrous (0.5 g) was added into AEAPMS (10 ml) with continuous stirring. The mixture was then transferred into an autoclave with a PTFE inner vessel and placed in 150° C. oven for 4 h. Brownish liquid was obtained after the reaction process. The product was dispersed in Milli-Q water or other appropriate solvent, followed by purifying three times with an $Al_2O_3$ filled chromatographic column in order to remove the residue reactants. The collected fraction was further filtered by a 0.22 μm syringe filter to remove the large particles. Finally, the solution was centrifuged for 30 min at 12000 rpm for further purification and the supernatant was collected as the product.

Example 2: Characterisation

OS-CDs prepared according to the synthetic procedure described in Example 1 were characterised as follows.

Figure 3:
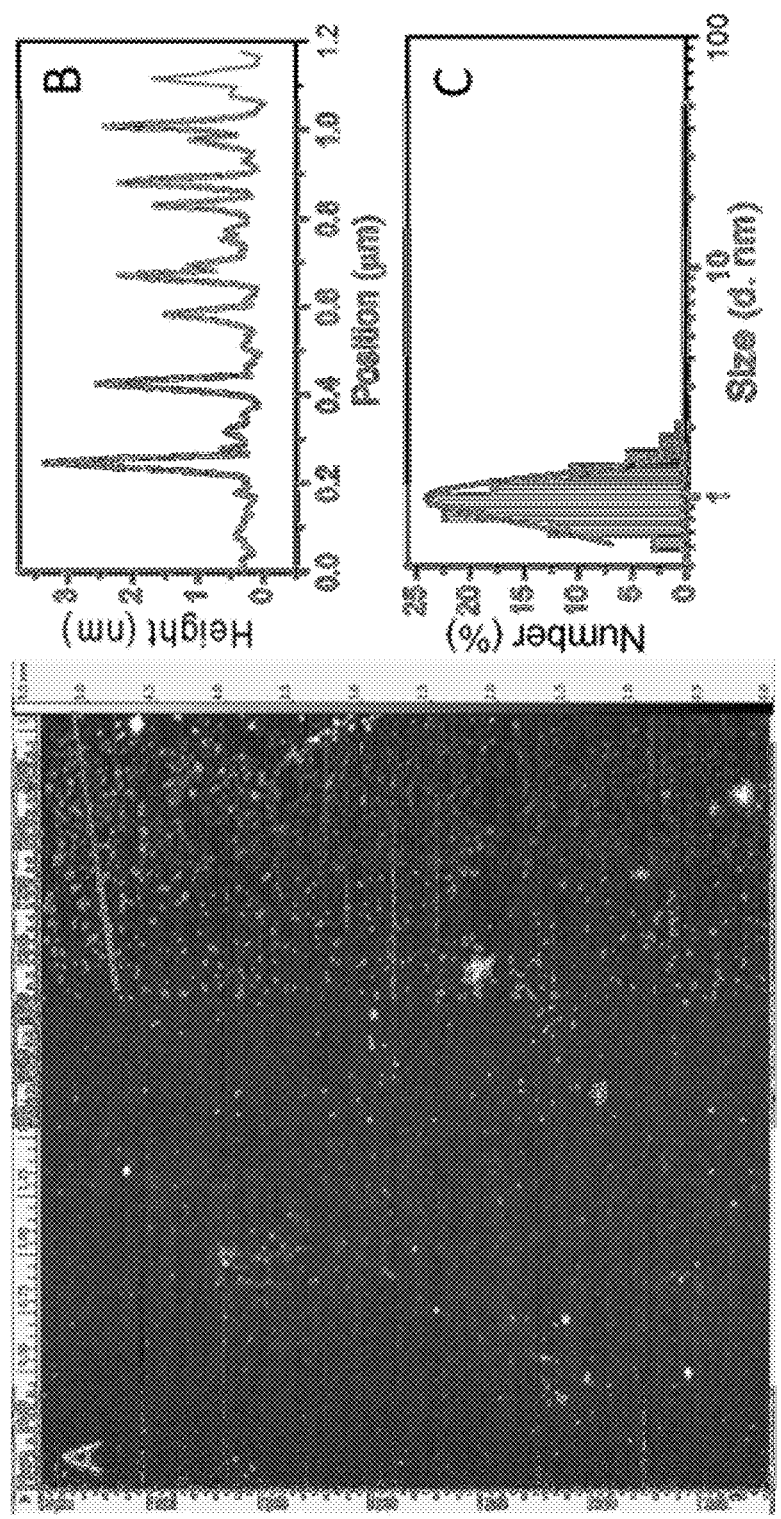
FIG. 3A is an atomic force microscopy (AFM) image of organosilane functionalised carbon nanoparticles (OS-CDs) prepared in accordance with one embodiment.
FIG. 3B is a graphic representation of the height profile of the OS-CDs shown in FIG. 3A along the line shown in FIG. 3A.
FIG. 3C is a graphical representation of size distribution of OS-CDs shown in FIG. 3A measured by diffractive light scattering (DLS) techniques.

The two-dimensional (2D) morphology of OS-CDs was characterised with atomic force microscopy (AFM, Dimension 3000) analysis, carried out with tapping mode on a platinum coated mica substrate (see FIG. 3A).

The height profile along the line shown in FIG. 3A is also depicted in FIG. 3B, indicating that the height of the OS-CDs ranges from 0.5 to 3 nm.

The hydrodynamic particle size was measured by dynamic light scattering (DLS) on a Malvern Instrument Zetasizer Nano-ZS at room temperature. The DLS analysis of a water diluted sample of the OS-CDs shows a narrow size distribution of 0.5-2 nm, as shown in FIG. 3C.

Figure 4:
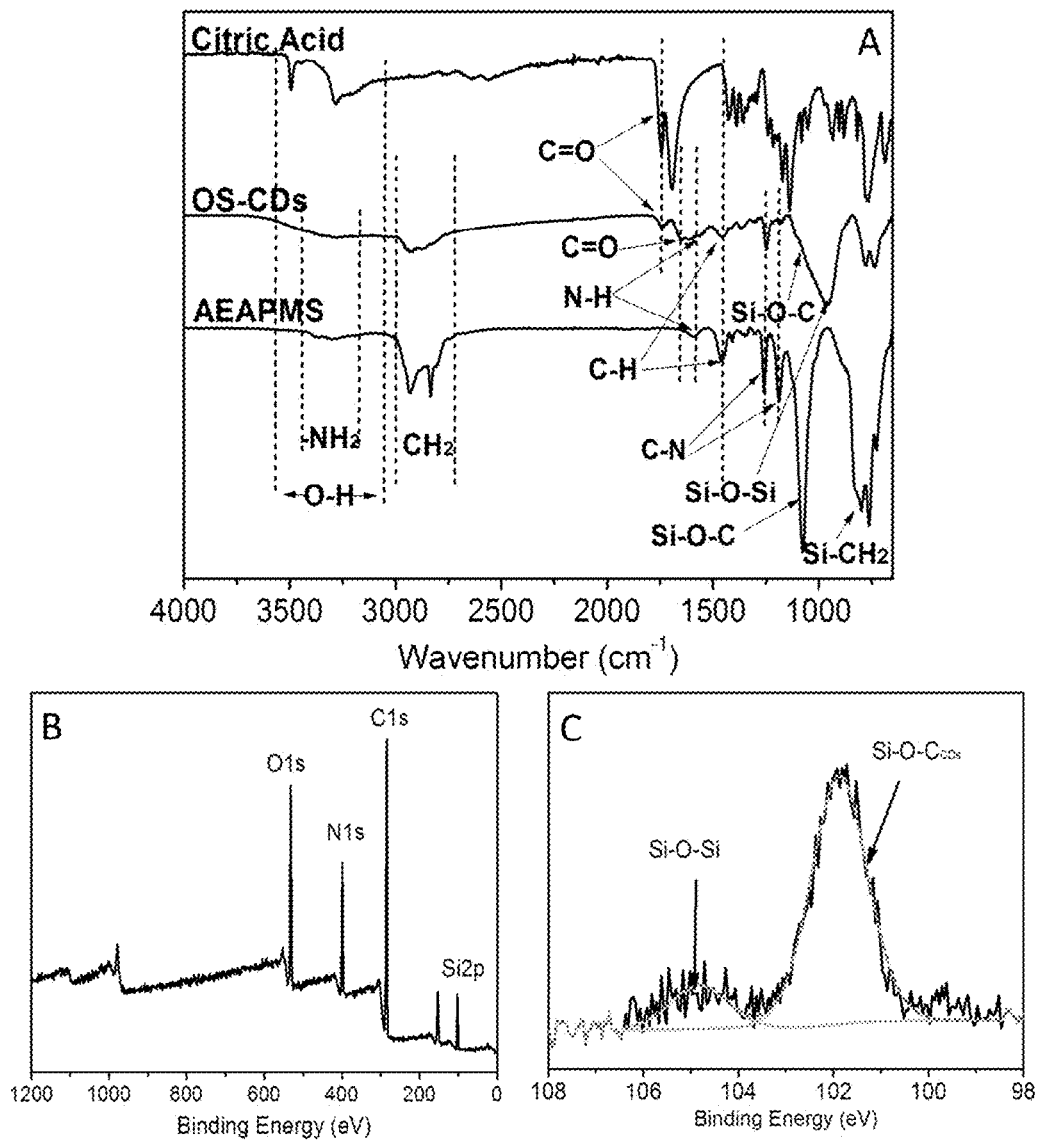
FIG. 4A is a Fourier Transform infrared (FTIR) spectra of citric acid, OS-CDs and N-(b-aminoethyl)-g-aminopropyl-methyl-dimethoxysilane (AEAPMS)
FIG. 4B is a surface scan of XPS spectra.
FIG. 4C is a high resolution spectra of Si 2p.

FT-IR spectra were collected on Perkin-Elmer Spectrum 100 with resolution of 4 $cm^{-1}$ in transmission mode at room temperature. A baseline correction was applied after the measurement. FIG. 4A shows the FT-IR spectra of the OS-CDs in comparison with the reactants, citric acid and AEAPMS. It is clear that C=O stretching vibration of the —COOH groups appeared at 1745 $cm^{-1}$ after the reaction. The broad absorption between 3200~3600 $cm^{-1}$ was attributed to hydroxyl groups or N—H. The peaks at 1630, 1565 and 1460 $cm^{-1}$ belonging to the C=O, N—H and C—H stretching of amide bond, respectively, suggest the formation of R—C=ONR between AEAPMS and carbon core, as illustrated by in FIG. 1. It should be highlighted that there is a distinctive, broad peak between 856 $cm^{-1}$ and 1140 $cm^{-1}$ which could be attributed to Si—O—Si and Si—O—C peaks, suggesting the formation of siloxane groups by hydrolization, which may lead to the attachment of organosilane long chain onto the carbon core surface, as illustrated in FIG. 1. The vibrational fingerprints of C—N(1180, 1250 $cm^{-1}$) and —$NH_2$ (3300 $cm^{-1}$) stretching vibration belonging to the amine-terminated long chains were both observed in the spectra of AEAPMS and the OS-CDs. The Si—O—Si and Si—O—C peaks as well as the terminal amine further confirm the attachment of amine-terminated long chains onto surface of the OS-CDs through hydrolization of organosilane.

X-ray photoelectron spectroscopic (XPS) measurements were performed on a Kratos Axis Ultra photoelectron spectrometer which uses Al Kα (1253.6 eV) x-rays. The XPS data shown in FIG. 4B reveals the elementary composition and atom percentages of OS-CDs, namely C 61.17%, N 13.93%, O 12.95% and Si 11.95%, confirming the framework of the OS-CDs are mainly constructed by carbon. High resolution spectrum of Si 2p was shown in FIG. 4C, the fitting peak at 101.9 eV is attributed to Si—O—$C_{CDs}$, suggesting the covalent attachment of silane end to the carbon core, and the peak at 104.9 eV is assigned to Si—O—Si of the silica network generated during the hydrolyzation of organosilane. High resolution spectra of C 1 s, N 1s and O1s detailing the chemical bonding states were also shown in FIG. 4B. In the C 1s spectra, the peak at 284.6 eV is assigned to C—C/C=C bonds of the framework, whereas the peaks at 285.6 eV and 287.8 eV can be attributed to C—N/C—O and C=O bond, respectively. N 1s spectra show peaks at 399.1 eV and 400.0 eV for C—N and —$NH_2$ respectively. In O1s spectra, peaks at 530.6 eV and 532.0 eV are ascribed to N—C=O and C—O, respectively.

Figure 5:
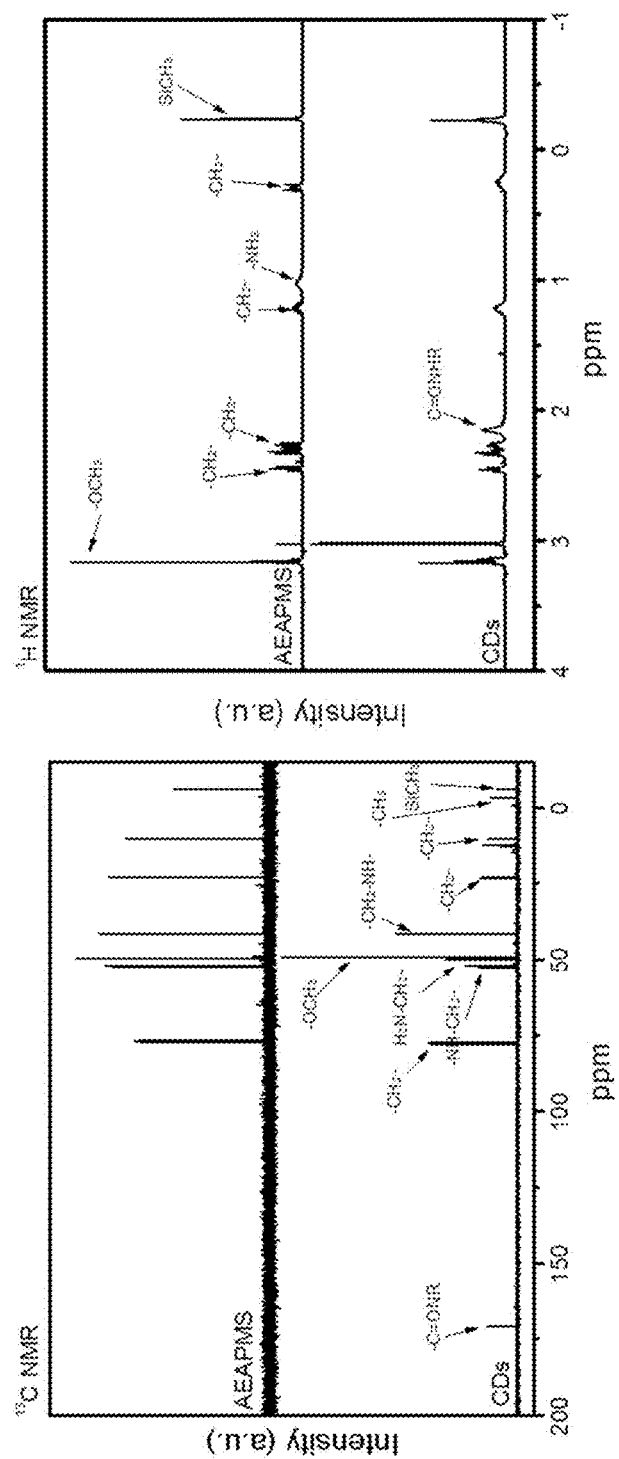
FIG. 5 shows $^{13}$C-NMR and $^{1}$H-NMR spectra of as-prepared OS-CDs and AEAPMS.

Nuclear Magnetic Resonance Spectroscopy (NMR) was performed on Agilent 600 MHz instrument equipped with a triple resonance $^1H$ ($^{13}C/^{15}N$) 5 mm cold probe. The NMR results in FIG. 5 confirm the formation of R—C=ONR group by amidation reaction through the peak of 171 ppm in $^{13}CNMR$. In addition, the intensity decrease of the H belonging to —$OCH_3$ group was observed in $^1HNMR$, indicating the decreased amount of —$OCH_3$ groups. This decrease can be attributed to the hydrolyzation of —Si($OCH_3$)$_2CH_3$ on carbon core surface in the presence of water, which was generated by the condensation of citric acid.

Overall, the chemical analyses have suggested that the solvothermal synthesized OS-CDs are constructed by mainly by carbon with dual long chains attached through R—C=ONR bond originated from amidation as well as Si—O—C and Si—O—Si bonding due to silane hydrolization on the surface of CDs as illustrated in FIG. 1. The co-existence of both amine terminated and $Si(OCH_3)_2CH_3$ terminated long chains on the surface of as-prepared OS-CDs afford them unique properties and functionalities.

Example 3: Optical Properties of OS-CDs

The absorption and emission was measured with a Jasco V670 UV-VIS spectrometer and a Thermal Scientific Lumina fluorescence spectrometer, respectively. Quantum yield was calculated using quinine sulphate as the reference probe.

Figure 6:
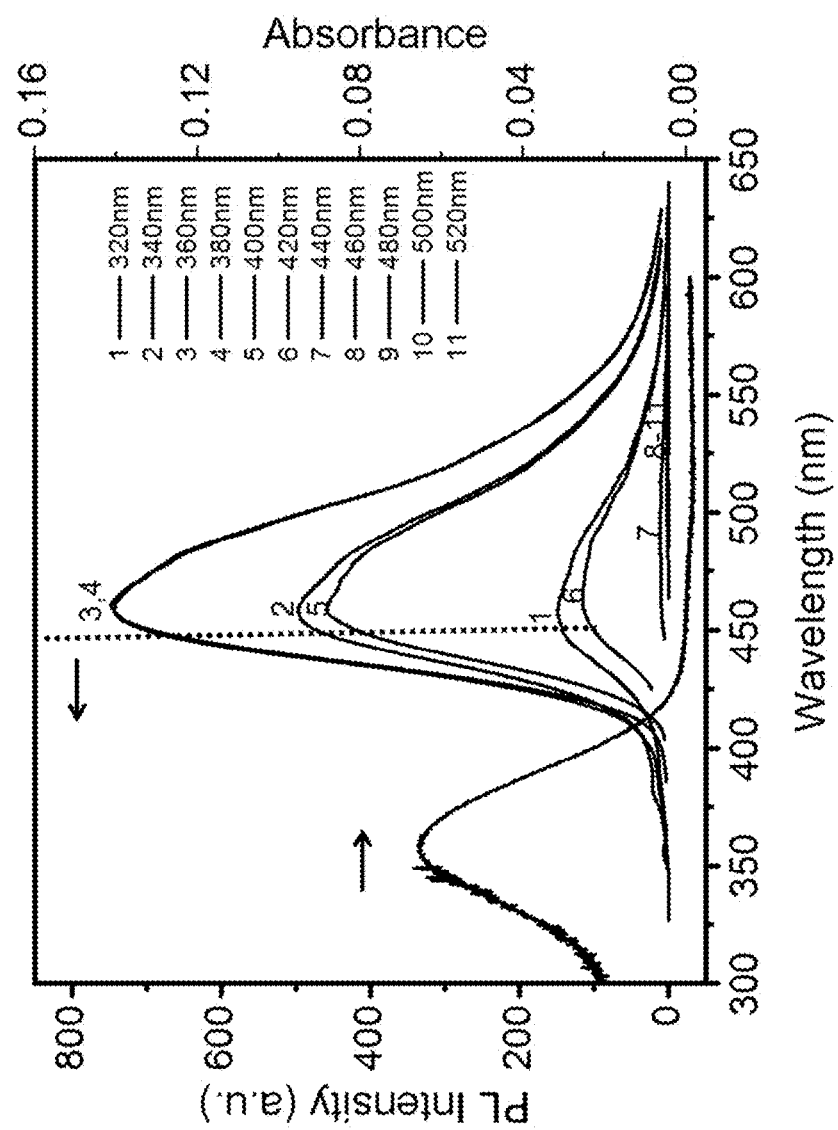
FIG. 6 shows UV-Vis absorption spectrum and photoluminescence emission spectra of OS-CDs at different excitation wavelengths.

The as-synthesized OS-CDs show a distinctive absorption peak centred at 360 nm in the UV-Vis absorption spectrum and maximum emission peaks at 465 nm in the emission spectra as shown in FIG. 6. In contrast to earlier reported OS-CDs, the as-prepared OS-CDs are excitation-independent. When the excitation wavelength was in range of 320~420 nm, no noticeable position shift in emission peaks was observed with the maximum emission wavelength remained at 465 nm. Further increasing excitation wavelength to 440 nm and above, the OS-CDs was almost non-fluorescent, indicating that only one fluorescence center dominates the fluorescence of these nanoparticles. The excitation-independence may also be ascribed to the narrow particle size distribution. 360 nm was selected as the excitation wavelength in the following experiment as it induced the highest fluorescent intensity of OS-CDs. The QY of the as-prepared OS-CDs in Milli-Q water is 51%, higher than most other reported CDs.

Figure 7:
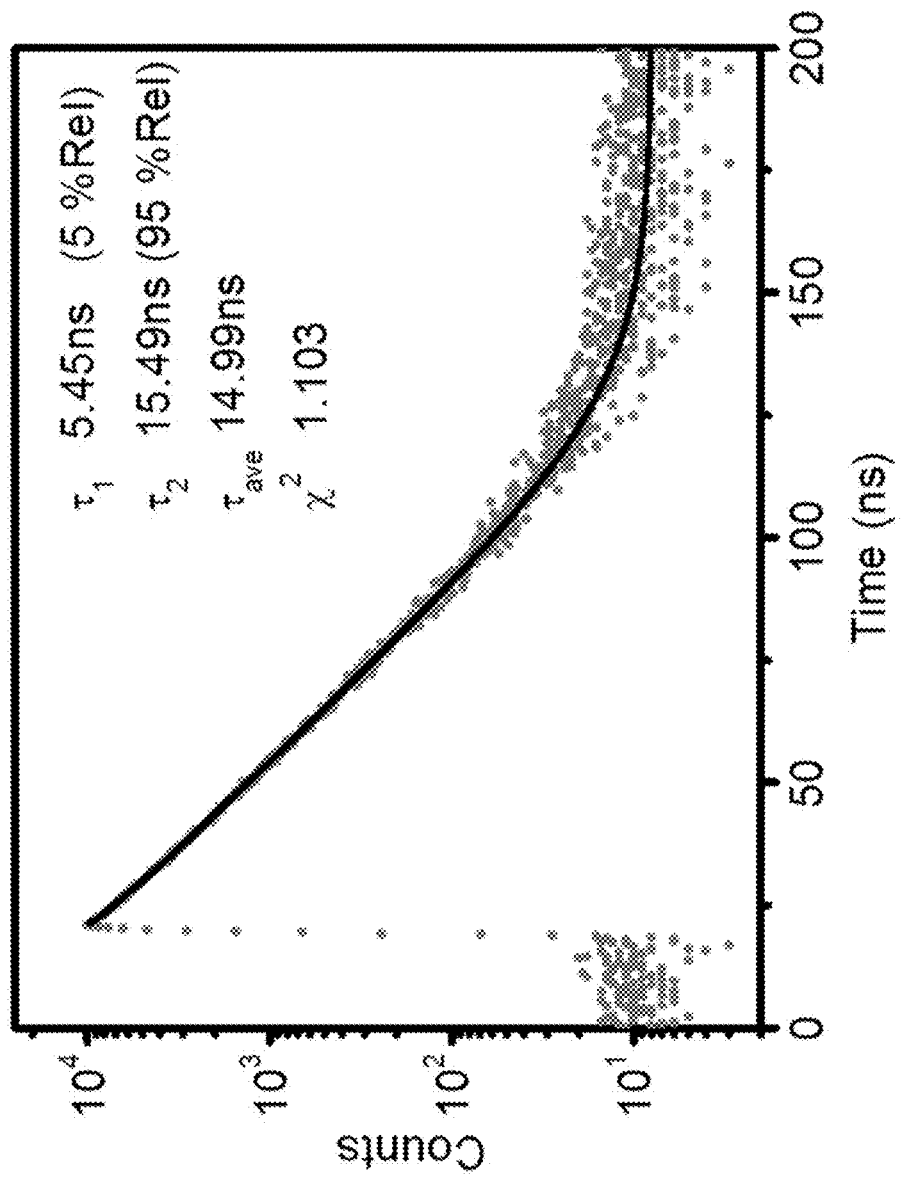
FIG. 7 shows the fluorescence lifetime of OS-CDs.

The fluorescence lifetime of OS-CDs in water under the excitation of 360 nm can be fitted by a multi-exponential function as shown in FIG. 7. Two fitting decay times were acquired, namely $\tau_1$=5.45 ns (5%) and $\tau_2$=15.49 ns (95%) with the average lifetime of 14.99 ns. Its extraordinary long fluorescence lifetime compared to the other CDs is likely due to the abundant long chain surface functional groups which provide better trapping effect.

Example 4: Amphiphilicity of OS-CDs

The dispersibility of OS-CDs in different solvents was examined by dropping 100 μL of OS-CDs into 5 ml of solvent, including DMSO, methanol, DMF, acetone, ethanol, THF, toluene and hexane as well as Milli-Q water, respectively, and mixed uniformly. The samples were kept at the room temperature for two weeks.

Figure 8:
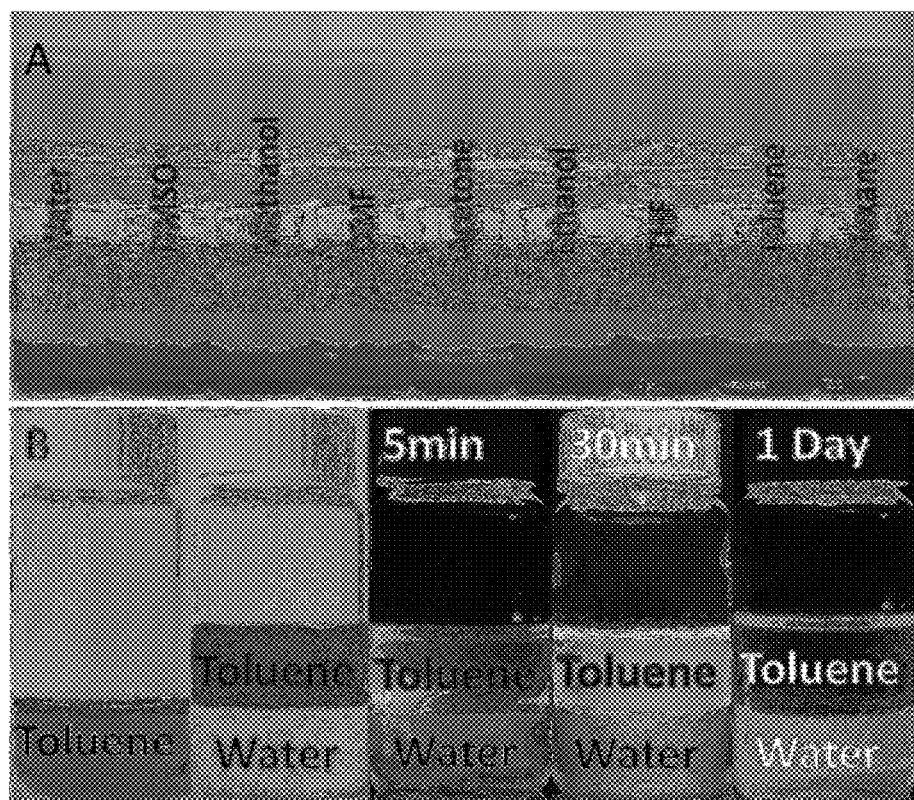
FIG. 8A shows the dispersion of OS-CDs in different solvents and FIG. 8B shows the amphiphillic performance of OS-CDs in toluene and water phase.

FIG. 8A shows that OS-CDs can be well dispersed in OS-CDs can be well dispersed in both polar and apolar solvents, including DMSO, methanol, DMF, acetone, ethanol, THF, toluene and hexane as well as Milli-Q water. No sediment or layering phenomenon were observed after two weeks, which shows the excellent multi-solvent solubility and stability.

The amphiphilicity of CDs was measured by dispersing 100 pt of OS-CDs into 5 ml toluene, and then slowly adding 5 ml of Milli-Q water into the above solution. An interface was clearly observed between water and toluene. The mixture was kept under UV to observe the movement of OS-CDs between organic solvent and water phase. The amphiphilicity of OS-CDs was vividly observed by mixing OS-CDs in toluene and water mixture, as shown in FIG. 8B. Fluorescence disappeared completely in the toluene phase but transferred into aqueous phase after 1 day, indicating the better solubility of OS-CDs in water than in toluene. The strong amphiphilicity of the as-synthesized OS-CDs further confirms the dual long chain surface chemistry illustrated in FIG. 1.

Example 5: Stability of OS-CDs

The thermal stability of OS-CDs in water at different temperature (25, 45, 65 and 85° C.) was investigated and the results were shown in FIGS. 9A and 9B. The photoluminescence of OS-CDs is very stable, showing reversible fluorescence after multiple cycles of temperature ramping from 25 to 85° C.

The photoluminescence intensity decreases with increasing solution temperature due to thermal diffusion and collision, as shown by the emission spectra of OS-CDs in FIG. 9A. However, when the temperature of solution was cooled down from 85 to 25° C., the photoluminescence intensity was restored to more than 95% of its original level after the first cycle. In the following temperature ramping cycles, the photoluminescence intensity did not change further as shown in FIG. 9B, with over 99% of the photoluminescence recovered in the following cycles. The photoluminescence thermal stability within the tested range from 25 to 85° C. indicates that the fluorescence quenching of OS-CDs under high temperature are mainly ascribed to the physical changes such as lower viscosity of solution, faster diffusion and hence larger amounts of collision between OS-CDs particles at high temperature, while the structure of the as-synthesized OS-CDs is well preserved in this process.

Figure 10:
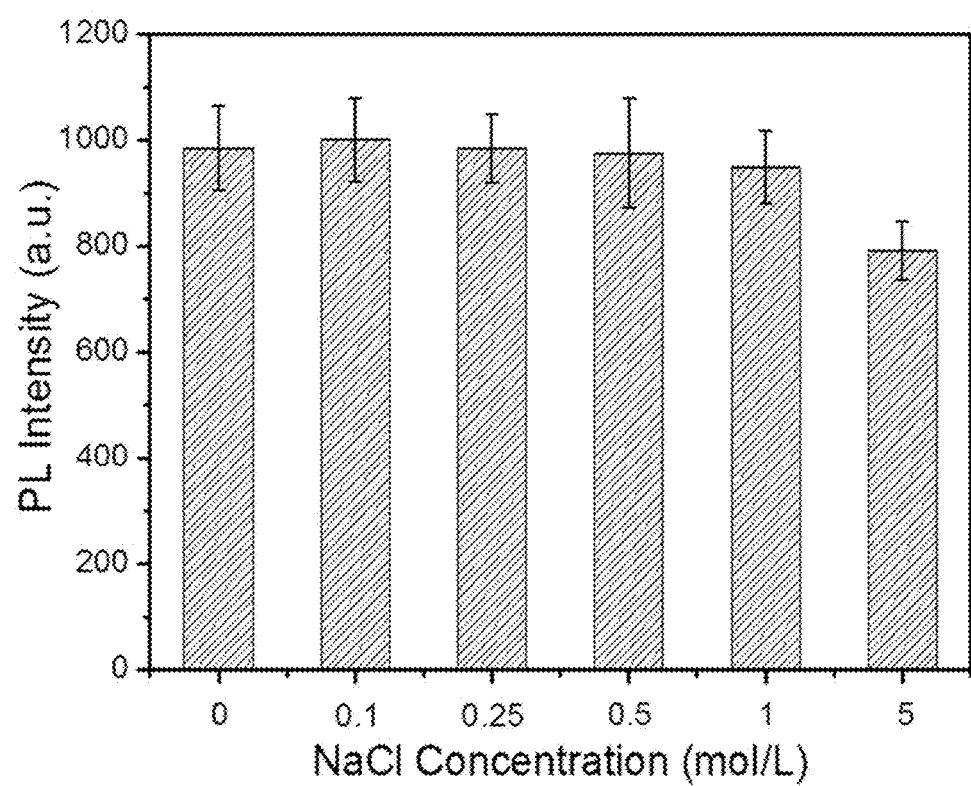
FIG. 10 shows the photoluminescence intensity of OS-CDs in NaCl solutions of different concentrations.

The photoluminescence intensity (see FIG. 10) does not vary when ionic strength is increased by adding NaCl up to 1 M. The excellent dispersity in solutions of high ionic strength can be ascribed to the steric effect due to the surface long chains.

Figure 11:
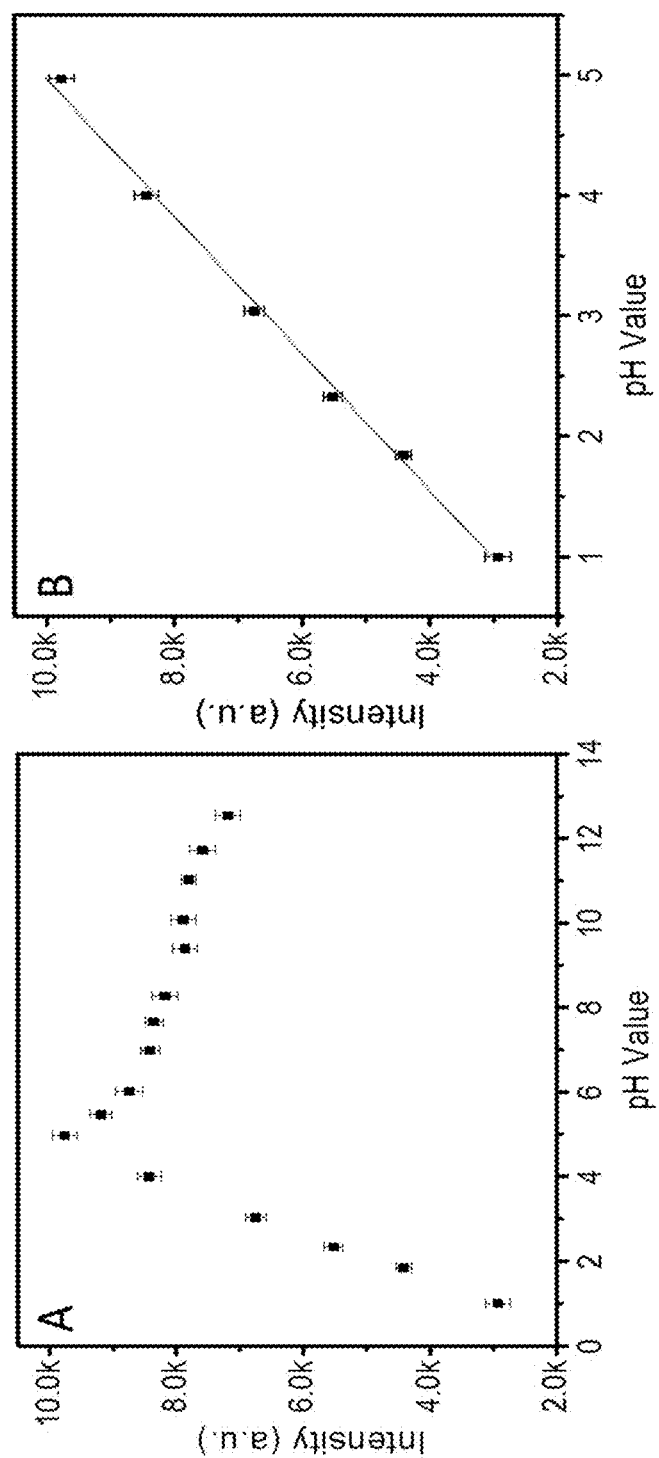
FIG. 11A shows the pH effect on photoluminescence intensity of as-prepared OS-CDs and FIG. 11B shows the linear fitting curve of pH value to photoluminescence intensity, wherein the error bars represent the standard deviation.

The fluorescence response of OS-CDs to the pH of a solution was also investigated. The as-synthesized OS-CDs possess pH-sensitive properties in weak acidic environment as shown in FIG. 11. As depicted in FIG. 11A, the OS-CDs showed reduced photoluminescence intensity at lower pH. The photoluminescence intensity increased linearly with the increase of pH from 1 to 5 (adjusted by adding NaOH), indicating the quenching effect of acidity. The further increase of pH from 5 to 12.6 leaded to a gradual decrease of photoluminescence intensity. FIG. 11B shows the linear fitting of pH value versus photoluminescence intensity, with the pH value in range of 1 to 5. The correlation coefficient $R^2$ of the fitting curve is 0.9942, indicating the goodness of the fit on the relationship between pH and photoluminescence intensity. The inventors postulate that the sensitivity of as-prepared OS-CDs to pH is due to the protonation and deprotonation of —$NH_2$ terminal group on the long functional chain. As mentioned earlier, this orientation of the organosilane chain with —$NH_2$ towards outside is a result of solvothermal synthesis, in contrast to the OS-CDs synthesized by 'hot injection'. Such pH sensitivity was not observed with OS-CDs before. This result suggests that the as-prepared OS-CDs can also be used as a simple pH probe for weak acidic solutions.

Example 6: $Hg^{2+}$ Detection in Pure Water

Figure 12:
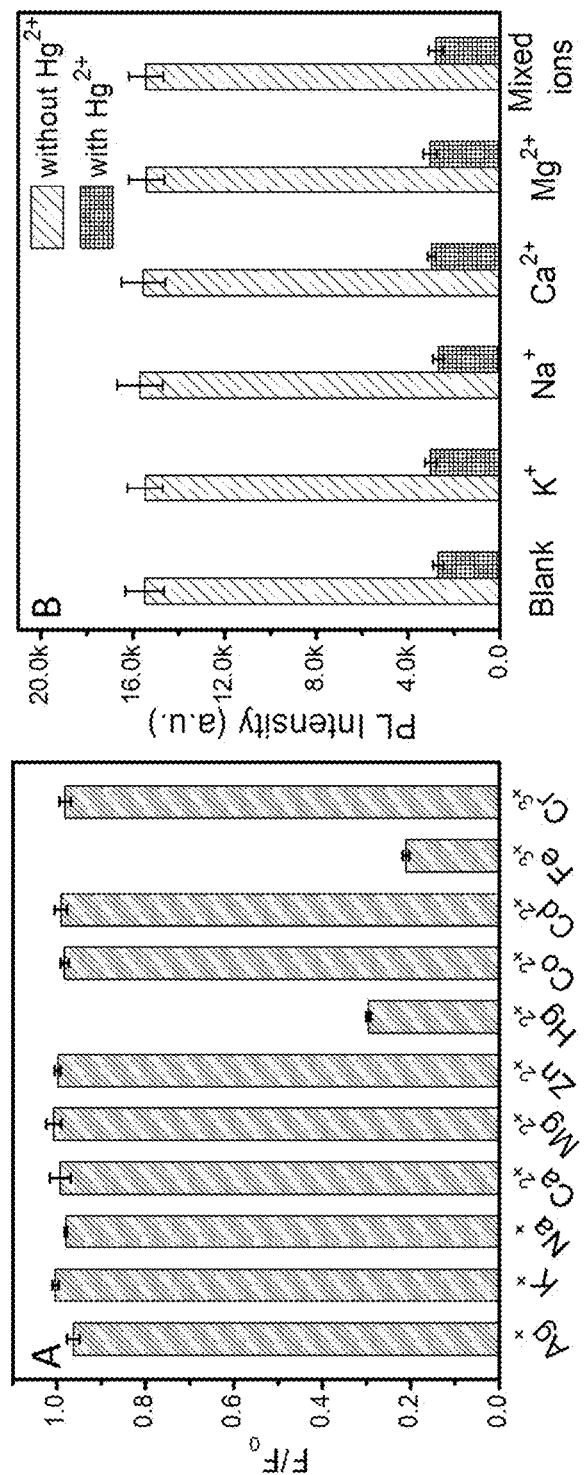
FIG. 12A shows the effect of metal ions (100 µM) on the fluorescence of OS-CDs and FIG. 12B shows the photoluminescence intensity of OS-CDs in water, $K^+$, $Na^+$, $Ca^{2+}$ and $Mg^{2+}$ aqueous (100 µM) with and without $Hg^{2+}$ ions, mixed ions including $K^+$, $Na^+$, $Ca^{2+}$ and $Mg^{2+}$, with the concentration of 100 µM.

The as-synthesized OS-CDs fluorescence sensitivity to metal cations were first assessed by adding a series of 100 μM aqueous solutions containing $Ag^+$, $K^+$, $Na^+$, $Ca^{2+}$, $Mg^{2+}$, $Zn^{2+}$, $Cu^{2+}$, $Hg^{2+}$, $Co^{2+}$, $Cd^{2+}$, $Fe^{3+}$ and $Cr^{3+}$. As shown in FIG. 12A, the photoluminescence of the OS-CDs was insensitive to most of the metal cations other than $Hg^{2+}$ and $Fe^{3+}$.

Figure 13:
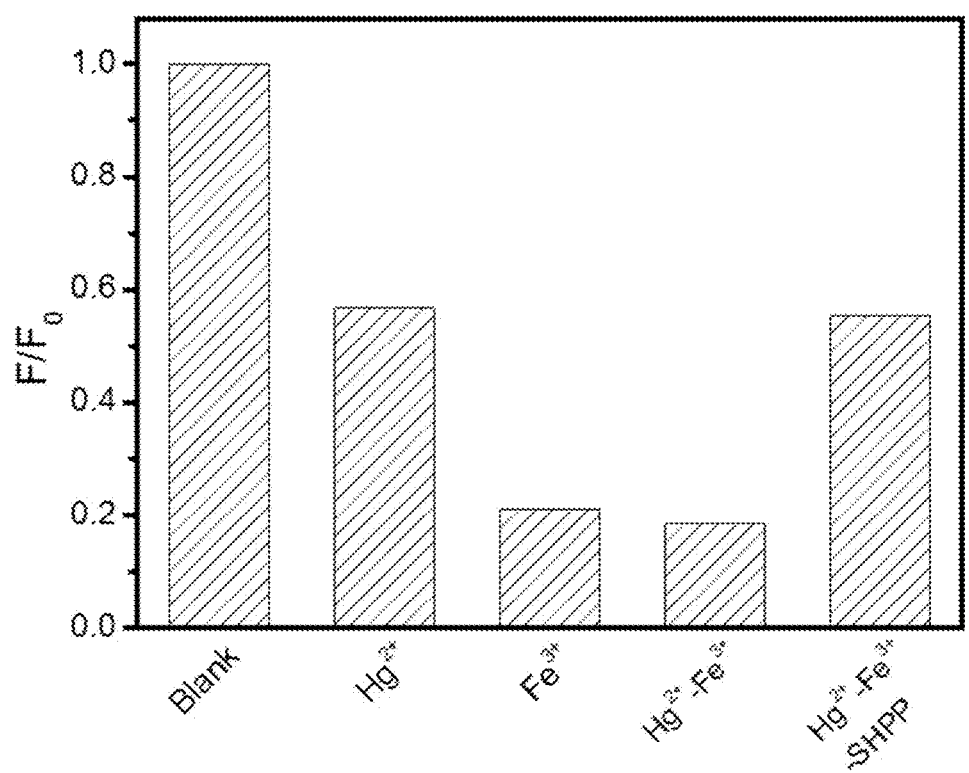
FIG. 13 shows the photoluminescence intensity of OS-CDs in water, and aqueous solutions containing $Hg^{2+}$, $Fe^{3+}$, $Hg^{2+}$—$Fe^{3+}$ and $Hg^{2+}$—$Fe^{3+}$- sodium hexametaphosphate (SHPP); wherein $[Hg^{2+}]=1$ µM, $[Fe^{3+}]=100$ µM, $[SHPP]=1$ mM.

Although $Fe^{3+}$ also induced the fluorescence quenching of OS-CDs, $Hg^{2+}$ can be selectively identified by adding sodium hexametaphoshpate as the masking agent of $Fe^{3+}$ ions as shown in FIG. 13.

To further verify the effect of the co-presence of some common mineral elements such as $K^+$, $Na^+$, $Ca^{2+}$ and $Mg^{2+}$ on OS-CDs' sensing selectivity to $Hg^{2+}$, the photoluminescence intensities of OS-CDs in pure water, and in solutions containing $K^+$, $Na^+$, $Ca^{2+}$, $Mg^{2+}$ and a mixture of all above (100 μM) with and without $Hg^{2+}$ were compared as shown in FIG. 12B. The result clearly demonstrates that the presence of one or more above common metal ions has no adverse impact on OS-CDs's sensitivity to $Hg^{2+}$ ions. In addition, anions such as $SO_4^{2-}$, $NO_3^-$, $Cl^-$ and $C_2O_4^{2-}$ were found to have no effect on the fluorescence of OS-CDs (data not shown). All these lead to the conclusion that the as-prepared OS-CDs possess excellent selectivity to $Hg^{2+}$.

Figure 14:
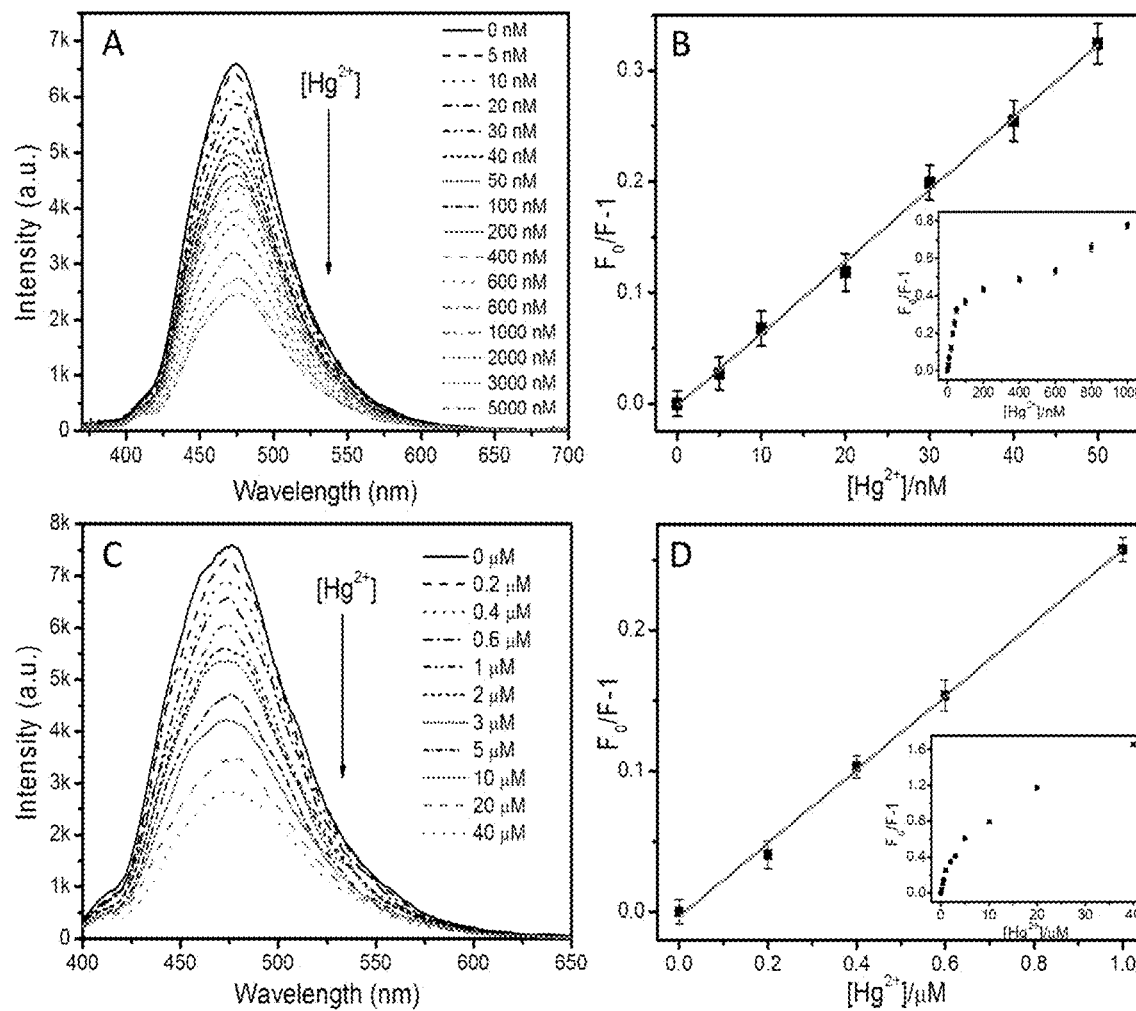
FIG. 14A shows emission spectra of OS-CDs in water with different $Hg^{2+}$ concentrations of 0~5 µM.
FIG. 14B shows the linear region of Stern-Volmer plot within the range of 0~50 nM and the Inset shows the relationship between $F_0/F-1$ and $Hg^{2+}$ concentrations within the range of 0~1 µM.
FIG. 14C shows emission spectra of OS-CDs in waste water with different concentrations of $Hg^{2+}$ in range of 0~40 µM.
FIG. 14D shows the linear region of Stern-Volmer plot within the range of 0~1 µM and the Inset shows the relationship between $F_0/F-1$ and $Hg^{2+}$ concentrations within the range of 0~40 µM.

The sensitivity of the as-prepared OS-CDs to $Hg^{2+}$ concentration in the range of 0~5 μM was evaluated. As shown in FIGS. 14A and 14B, concentration-dependent quenching was observed: with the increase of $Hg^{2+}$ concentration from 0 to 5 μM, the photoluminescence intensity decreased gradually. The fluorescence quenching data can be fitted by the Stern-Volmer equation:

$$\frac{F_0}{F} - 1 = K_{SV} c$$

where $K_{sv}$ is the Stern-Volmer quenching constant, c is the concentration of $Hg^{2+}$, $F_0$ and F is the PL intensity of OS-CDs without $Hg^{2+}$ and with different concentration of $Hg^{2+}$, respectively. As shown in FIG. 14B, a good linear correlation ($R^2=0.9977$) was obtained over the concentration range of 0~50 nM, with a quenching constant $K_{sv}$ of $6.49 \times 10^{-3}$ L/mol.

Figure 15:
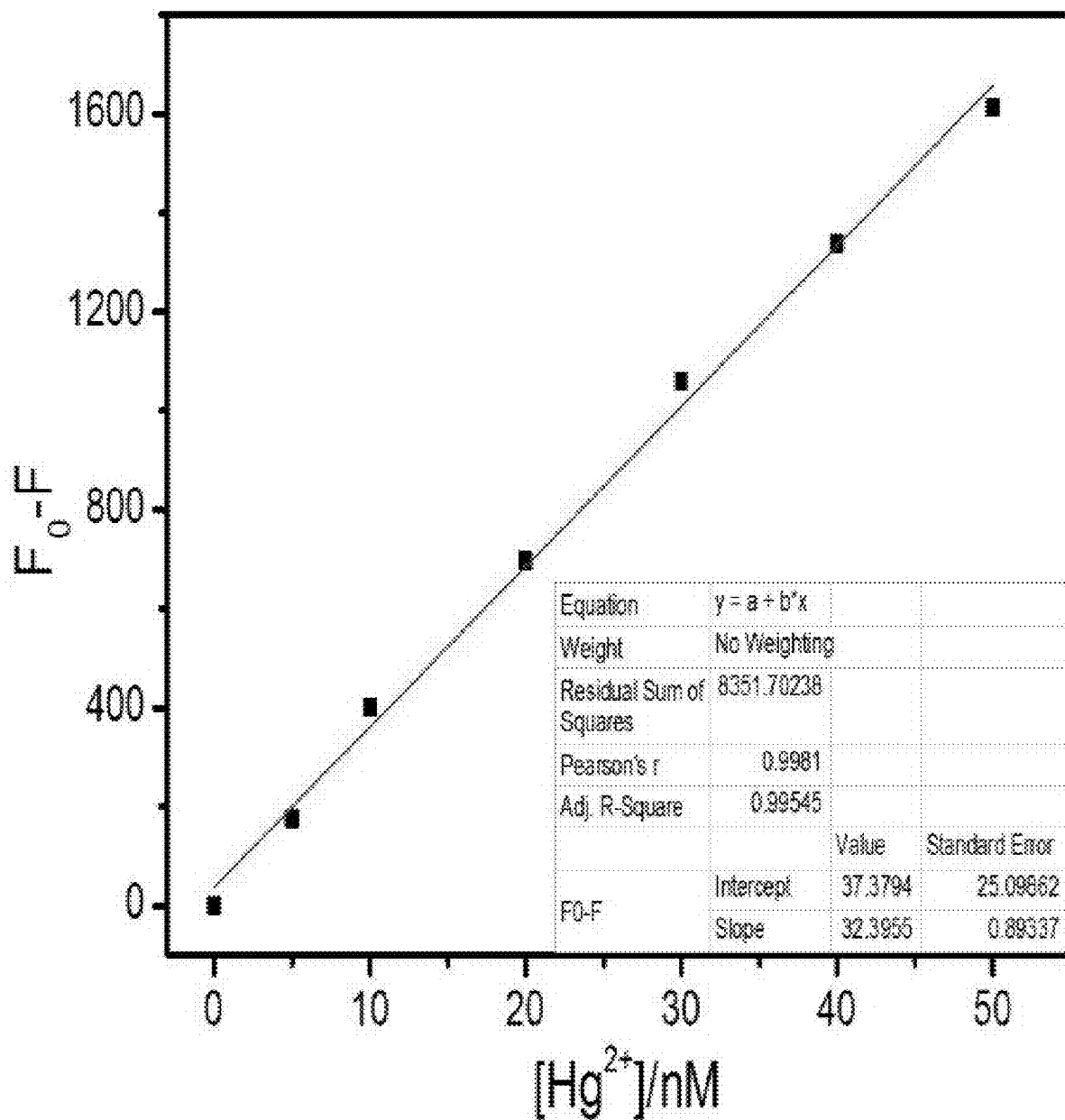
FIG. 15 shows the fluorescence quenching value $(F_0-F)$ vs. $Hg^{2+}$ concentration.

The detection limit of $Hg^{2+}$ was calculated with the following equation: 3σ/m, where m is the slope of fit curve of the fluorescence quenching values ($F_0$–F) vs. $Hg^{2+}$ concentration. σ is the standard deviation of the fluorescence of the sample without addition of $Hg^{2+}$. As shown in FIG. 15, the m value was obtained to be 32.4, σ (averaged from nine times measurement) was obtained to be 43.85. The detection limit was thus calculated to be 1.35 nM.

Figure 16:
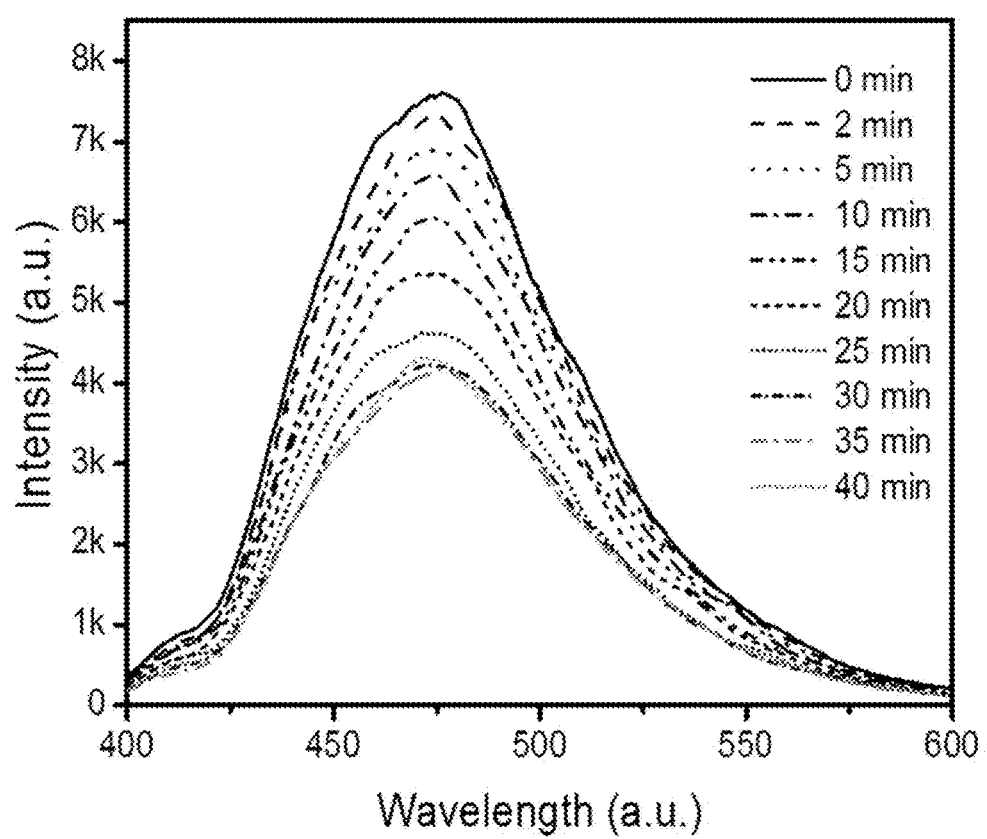
FIG. 16 shows the time-dependent quenching of OS-CDs by 0.5 µM $Hg^{2+}$.

The time-dependant quenching of OS-CDs was observed as shown in FIG. 16, indicating 30 min was required for the complete interaction between OS-CDs and $Hg^{2+}$ ions due to a slow diffusion.

Example 7: $Hg^{2+}$ Detection in Saline Water

Figure 17:
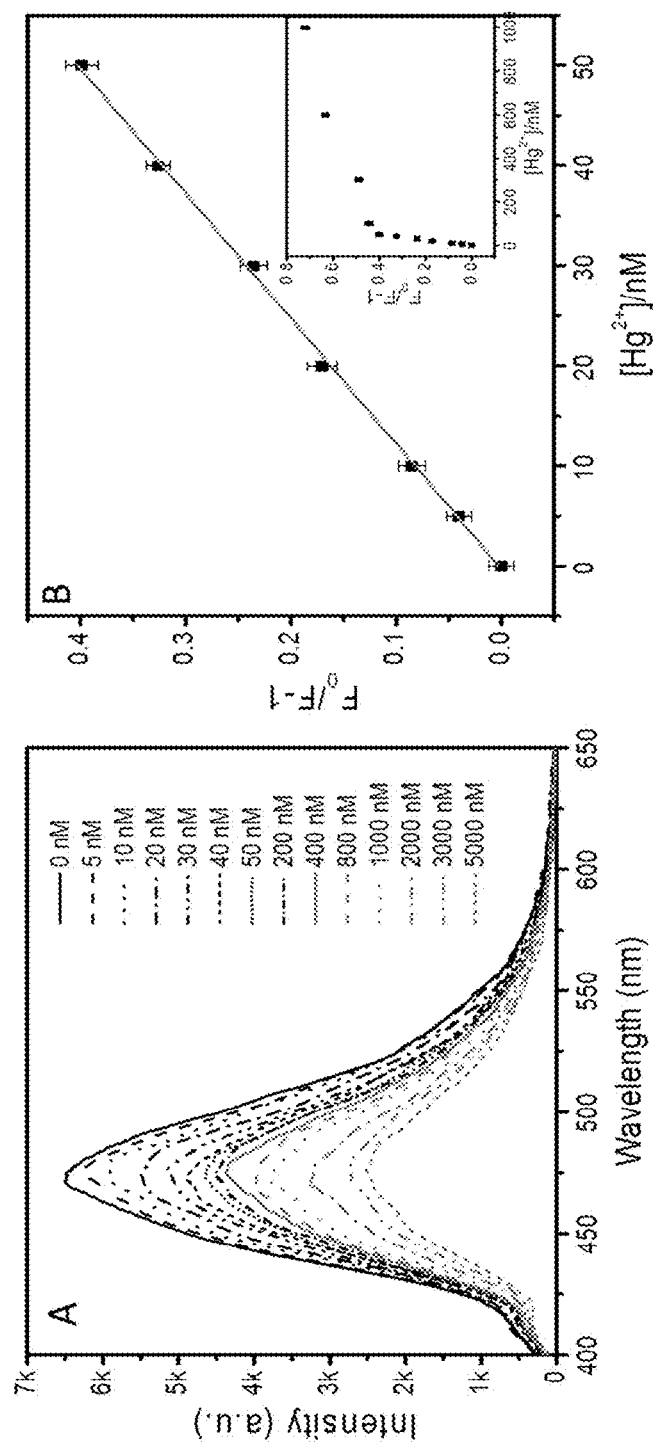
FIG. 17A shows the emission spectra of OS-CDs in saline solution (in 1M NaCl) in the presence of different concentrations of $Hg^{2+}$ in range of 0~5 µM.
FIG. 17B shows the linear region of Stern-Volmer plot within the range of 0~50 nM; and the Inset shows the relationship between $F0/F-1$ and $Hg^{2+}$ concentrations within the range of 0~1 µM.

The high ionic strength photoluminescence stability of OS-CDs is highly desirable in practical applications such as water quality measurement at mining sites. Therefore, the sensitivity of OS-CDs to $Hg^{2+}$ ions in saline solutions (with NaCl concentration of 1 M) were evaluated. As shown in FIG. 17, the photoluminescence of the as-prepared OS-CDs maintains excellent response to the concentration of $Hg^{2+}$ in the range of 0~50 nM with a good linearity ($R^2=0.9987$). The detection limit was determined as 1.7 nM, very close to the result in pure water, confirming the stability of OS-CDs in solutions of high ionic strength as a result of the steric effect.

Example 8: $Hg^{2+}$ Detection in Municipal Wastewater

The fluorescence quenching of OS-CDs by different concentration of $Hg^{2+}$ in the wastewater sample were investigated. Wastewater after secondary treatment which contains many kinds of bacteria, viruses, metal ions and fluorescent organic molecules, was the sample. As shown in FIGS. 14C and 14D, the OS-CDs can still detect the $Hg^{2+}$ ions from 0.2 μM to 40 μM. The Stern-Volmer plot show the linear range of 0 to 1 μM with $R^2=0.9978$ and $K_{sv}=0.26$ L/mol. The detection limit for $Hg^{2+}$ in wastewater was calculated to be 50 nM, highly sensitive for wastewater quality monitoring. The preserved excellent $Hg^{2+}$ sensitivity in wastewater effluent suggests the as-synthesized OS-CDs are largely non-interactive with the microorganisms and organic molecules in wastewater, owing to the negative charge, long chain surface functional groups. The slight loss of $Hg^{2+}$ sensitivity of OS-CDs in wastewater is likely due to the high background fluorescence caused by the organic molecules in wastewater.

Example 9: Reversible $Hg^{2+}$ Binding

CDs-coated PS spheres (PSCDs) were obtained by a diffusion and entrapment method through the addition of OS-CDs in dimethyl formamide (DMF) to an aqueous suspension of 150 μL of functionalized 230 nm PS spheres followed by the removal of DMF. A volume of 300 μL of OS-CDs in DMF was added drop-wise to the swelled 230 nm PS suspension until the DMF content reached 30 vol. %. The PSCDs were self-assembled into a film and dried.

Figure 18:
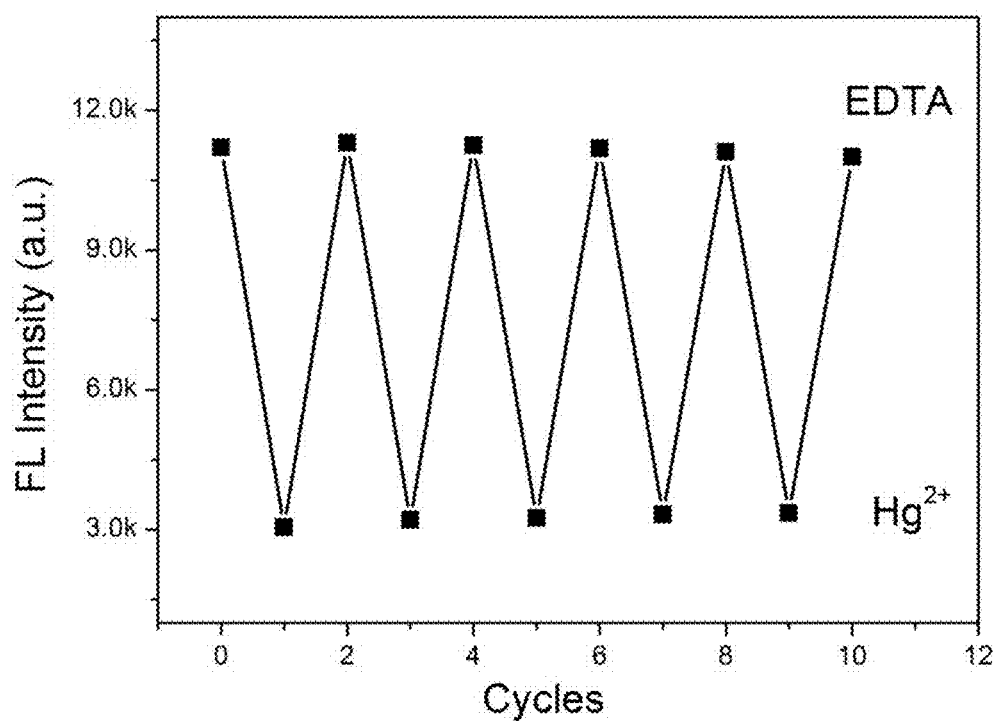
FIG. 18 is a graph showing reversible changes of the FL intensities of the film sensor when immersed in a solution of 1.0 nM $Hg^{2+}$ ions and 2 mM EDTA alternately.

FIG. 18 shows the fluorescence intensities of the film sensor at 600 nm when immersed alternately in the solutions of 1.0 nM Hg2+ ions and 2 mM EDTA solution for 5 min at room temperature, then washed with deionised water to recover to the blank state for ten regeneration cycles which indicates that the sensor has good recoverability and reproducibility without degradation of the response time or significant change in FL intensities. A single film sensor film was used throughout a sequent investigation. The reason for the suspended CDs having irreversibility (against EDTA) is thought to be that the neighbouring functional groups on the CDs form cage effect in capturing Hg(II) as illustrated in FIG. 2.

Example 11: Types of Device

Figure 19:
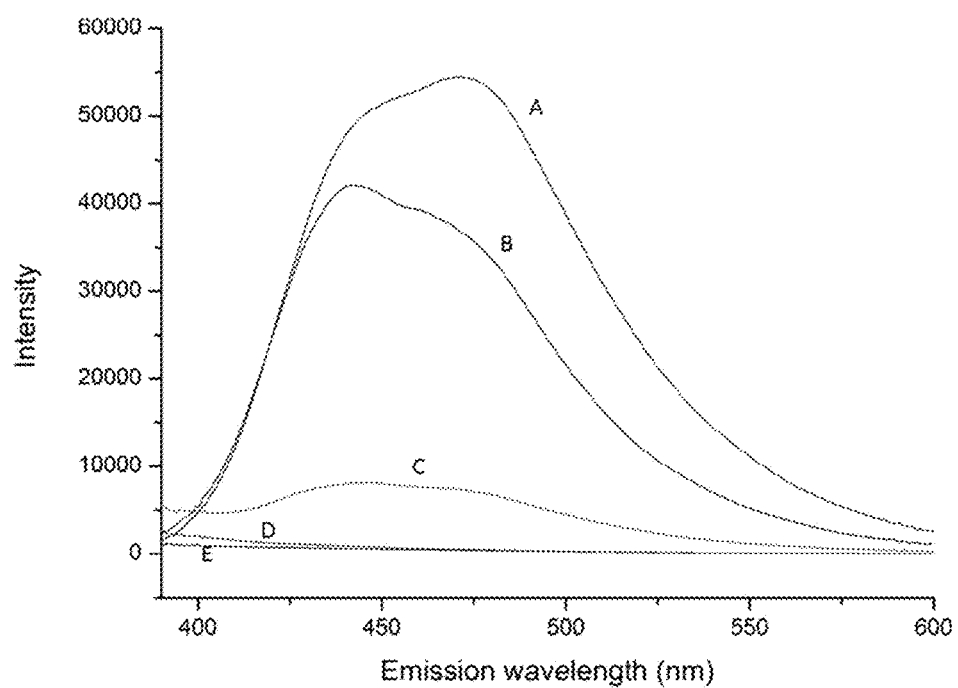
FIG. 19 is a graph showing the emission of OS-CDs in solid state after being immobilized on solid substrate

FIG. 19 is a graph showing the OS-CDs are emissive in solid state after being immobilized on solid substrate, this case glass. The curves show E, a blank glass slip; D a glass slip coated with saline; C a glass slip coated with CD modified silica spheres; B a glass slip coated with a mixture of saline and CD; and A a glass slip coated with CD-EtOH solution (dried).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Further, with regard to the various means referred to throughout the specification, any means is to be understood as encompassing individual as well as plural structures that may or may not be physically connected.

The invention claimed is:

1. Organosilane functionalised carbon nanoparticles comprising a carbon dot bonded to a first organosilane functionalization agent, the organosilane functionalization agent having a free end and a fixed end, wherein the organosilane functionalization agent is bonded to the carbon dot in a first orientation in which one or more functional groups capable of binding mercury are located at or proximal to the free end and the fixed end of the organosilane functionalization agent is bonded to the surface of the carbon dot with Si—O—Si and/or Si—O—C bonds; and
   a second organosilane functionalization agent that neighbors the first organosilane functionalization agent and has a functional group that neighbors the functional group in the first organosilane functionalization agent, wherein the neighboring functional groups from the neighboring organosilane functionalization agents together form a coordinating cage that binds mercury.

2. The nanoparticles according to claim 1, wherein the one or more functional groups capable of binding to mercury is an N-containing functional group and/or S-containing functional group.

3. The nanoparticles according to claim 2, wherein at least one of the one or more functional groups capable of binding mercury is an N-containing functional group that comprises an amine group.

4. The nanoparticles according to claim 2, wherein at least one of the one or more functional groups capable of binding mercury is an S-containing functional group that comprises a thiol group.

5. The nanoparticles according to claim 2, wherein the N-containing functional groups comprises a chelating amine group.

6. The nanoparticles according to claim 2, wherein the N-containing functional groups comprises an imidazolidone group.

7. The nanoparticles according to claim 1, in which the first organosilane functionalization agent is bonded to the carbon dot in a second orientation in which the fixed end of the organosilane functionalization agent is bonded to the surface of the carbon dot at or proximal to the one or more functional groups, and one or more silane functional groups of the first organosilane functionalization agent are located at or proximal to the free end.

8. The nanoparticles according to claim 7, wherein in the second orientation, the fixed end of the first organosilane functionalization agent is bonded to the surface of the carbon dot via the one or more functional groups.

9. The nanoparticles according to claim 1, wherein said nanoparticles are amphiphilic.

10. The nanoparticles according to claim 1, wherein said nanoparticles are dispersible in polar and apolar solvents.

11. The nanoparticles according to claim 1, wherein said nanoparticles are photoluminescent.

12. The nanoparticles according to claim, 11 having a quantum yield >20%.

13. The nanoparticles according to claim 12, having a quantum yield >40%.

14. The nanoparticles according to claim 11, wherein said nanoparticles are excitation-independent.

15. The nanoparticles according to claim 11, wherein the photoluminescence of said nanoparticles is quenched in the presence of mercury.

16. The nanoparticles according to claim 15, wherein the organosilane functionalized carbon nanoparticles have a detection range of 0-50 nM $Hg^{2+}$.

17. The carbon nanoparticles according to claim 16, wherein the organosilane functionalized carbon nanoparticles have a detection limit of <2 nM $Hg^{2+}$.

18. The carbon nanoparticles according to claim 17, wherein the organosilane functionalized carbon nanoparticles have a detection limit of 1.35 nM $Hg^{2+}$.

19. A photoluminescent sensor for mercury comprising the organosilane functionalized carbon nanoparticles as defined in claim 1.

* * * * *

UNITED STATES PATENT AND TRADEMARK OFFICE
CERTIFICATE OF CORRECTION

PATENT NO. : 10,502,686 B2
APPLICATION NO. : 15/323467
DATED : December 10, 2019
INVENTOR(S) : Qin Li et al.

Page 1 of 1

It is certified that error appears in the above-identified patent and that said Letters Patent is hereby corrected as shown below:

In the Claims

At Column 21, Line 21, "wherein" should be -- wherein at least one of --.

At Column 21, Line 23, "and/or S-containing" should be -- and/or an S-containing --.

At Column 21, Line 34, "groups" should be -- group --.

At Column 21, Line 37, "groups" should be -- group --.

At Column 22, Line 18, "claim, 11" should be -- claim 11, --.

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*